United States Patent
Choe et al.

(10) Patent No.: US 7,262,164 B2
(45) Date of Patent: Aug. 28, 2007

(54) POLYMERIC THIOL-LINKED PRODRUGS EMPLOYING BENZYL ELIMINATION SYSTEMS

(75) Inventors: Yun H. Choe, Green Brook, NJ (US); Richard B. Greenwald, Somerset, NJ (US)

(73) Assignee: Enzon, Inc., Bridgewater, NJ (US)

( * ) Notice: Subject to any disclaimer, the term of this patent is extended or adjusted under 35 U.S.C. 154(b) by 458 days.

(21) Appl. No.: 10/290,694

(22) Filed: Nov. 8, 2002

(65) Prior Publication Data

US 2003/0157052 A1 Aug. 21, 2003

Related U.S. Application Data

(60) Provisional application No. 60/344,912, filed on Nov. 9, 2001, provisional application No. 60/367,320, filed on Mar. 25, 2002.

(51) Int. Cl.
*A61K 38/16* (2006.01)

(52) U.S. Cl. .............................. 514/8; 514/2; 424/432; 424/54.21

(58) Field of Classification Search .................... 514/8, 514/2; 525/432, 54.21; 424/78.17
See application file for complete search history.

(56) References Cited

U.S. PATENT DOCUMENTS

| | | | | |
|---|---|---|---|---|
| 3,091,623 A * | 5/1963 | Knox, Jr. et al. | .............. | 554/57 |
| 4,772,586 A * | 9/1988 | Manning et al. | .............. | 514/11 |
| 5,112,739 A | 5/1992 | Meneghini et al. | | |
| 6,255,361 B1 * | 7/2001 | Rajagopalan et al. | ......... | 521/97 |

FOREIGN PATENT DOCUMENTS

| WO | WO96/23794 | * | 8/1996 |
|---|---|---|---|
| WO | WO/00/67801 | | 11/2000 |

OTHER PUBLICATIONS

Royer et al., Journal of the American Chemical Society, 1979, vol. 101(12), pp. 3394-3396.*

Woghiren, Clement, et al. Protected Thiol-Polyethylene Glycol: A New Activated Polymer for Reversible Protein Modification, Bioconjugate Chem. 1993, 4, 314-318.

Modica, Emilia et al., Alkylation of Amino Acids and Glutathione in Water by o-Quinone Methide. Reactivity and Selectivity, J. Org. Chem. 2001, 66, 41-52.

Bogardus, Joseph B., et al., Kinetics and Mechanism of Hydrolysis of Labile Quaternary Ammonium Derivatives of Tertiary Amines, Journal of Pharmaceutical Sciences, Jul. 1982, vol. 71 No. 7.

Harada, Naoyuki et al., Water-Soluble Antitumor Agents. I. Synthesis and Biological Activity of 6-S-Aminoacyloxymethyl Mercaptopurine Derivatives, Chem. Pharm. Bull. 43(10) 1793-1796 (1995).

Kashida, Tatsuo, Augmentation of Sinecomitant Immunity in Mice by y-(9H-Purine-6-yl) thiomethyl L-Glutamate (6-MPG), a Water-Soluble Derivative of 6-Mercaptopurine, Biol. Pharm. Bull. 21(1) 16-21 (1998).

Taylor, Lloyd D., Use of o-and p-Hydroxybenzyl Functions as Blocking Groups Which Are Removable with Base, J. Org. Chem., vol. 43, No. 6, 1978.

Wakselman, Michel, 1,4-And 1,6-Eliminations From Hydroxy- And Amino-Substituted Benzyl Systems: Chemical and Biochemical Applications, Nouveau Journal De Chime, vol. 7 Jul. 1983 p. 439-447.

* cited by examiner

*Primary Examiner*—B. Dell Chism
(74) *Attorney, Agent, or Firm*—Lucas & Mercanti, LLP

(57) ABSTRACT

Thiol-linked polymeric prodrugs, methods of making and using the same are disclosed. The use of a sulfhydryl bond in combination with a benzyl elimination system results in the formation of prodrugs which can take advantage of plasma enzymes in vivo for regeneration of the parent molecule. A preferred prodrug in accordance with the invention is:

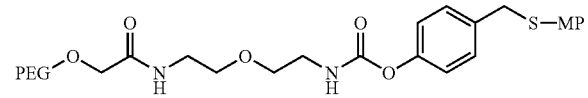

where S-MP is 6-mercaptopurine.

16 Claims, 11 Drawing Sheets

1: R = R' = H: 6-Mercaptopurine (HS-MP)

1b: R = H, R' = [ribose] : 6-Mercaptopurine Riboside (HS-MPR)

2: R = NH$_2$, R' = H: 6-thioguanine (HS-TG)

S-Drug =

PEG =

A. Dimeric conjugates.

C. Octameric conjugate.

POLYMERIC THIOL-LINKED PRODRUGS EMPLOYING BENZYL ELIMINATION SYSTEMS

CROSS-REFERENCE TO RELATED APPLICATIONS

This application claims the benefit of priority from U.S. Provisional Patent application No. 60/344,912, filed Nov. 9, 2001 and U.S. Provisional Patent application No. 60/367,320, filed Mar. 25, 2002. The contents of each provisional application are incorporated herein by reference.

TECHNICAL FIELD

The present invention relates to new types of long-acting, thiol-linked polymer conjugates of biologically-effective materials. In particular, the invention relates to polymer-based prodrug conjugates having enhanced water solubility, controlled pharmacokinetics and improved bioavailability, relative to the unmodified bioactive materials and methods of preparing the same.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. Simply by way of example, many of these biologically-effective materials have mercapto-functional groups. These include e.g., antiproliferative and/or immunosuppressive agents such as the mercaptopurines, as well as peptides and proteins with demonstrated or potential utility as medicinal agents. These types of materials often present complex problems of pharmacokinetics and bioavailability based on their poor solubility in blood or tissue fluids, tissue distribution, clearance rate and antigenicity, after administration to an animal in need of such treatment.

For instance, the class of compounds known as nucleoside and nucleotide analogs are potentially useful therapeutically in the treatment of cancers and in immuno-supression, because they interfere with DNA synthesis. This property is useful in treating a broad class of diseases or disorders characterized by excessive or inappropriate cell division. However, the artisan will appreciate that these compounds have a very narrow therapeutic index, requiring careful control of dose, kinetics and tissue concentrations. Thus, there is a need to provide improved nucleoside and nucleotide analogs where more targeted delivery to selected tissues, and/or improved release kinetics is desirable.

For example, 6-mercaptopurine or 6-MP, while otherwise a promising anticancer agent and immunosuppressive, has substantial drawbacks. Absorption of 6-MP is incomplete after oral ingestion and bioavailability is reduced by first-pass metabolism through the liver. It is reported that oral bioavailability of 6-MP is only 5% to 37%, with great variability between patients.

One way to solubilize biologically-effective materials and improve solubility, bioavailability, etc., is to include them as part of a soluble prodrug. Prodrugs include chemical derivatives of a medicinal agent, e.g., a biologically-effective parent compound which, upon administration, eventually liberates the parent compound in vivo. Prodrugs allow the artisan to modify the onset and/or duration of action of an agent, in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols.

Prodrugs are often biologically inert or substantially inactive forms of the parent or active compound. The rate of release of the active drug, typically by hydrolysis, is influenced by several factors, but especially by the type of bond joining the parent drug to the modifier. Care must be taken to avoid preparing prodrugs which are eliminated through the kidney or reticular endothelial system, etc., before a sufficient amount of hydrolysis of the parent compound occurs.

Previous efforts to improve the utility of certain therapeutically useful mercaptan compounds have been reported. For example, azathioprine (IMURAN) is a prodrug of 6-mercaptopurine containing an imidazole group attached to the sulfur at the 6-position of the purine ring. This substitution serves to decrease the rate of inactivation by enzymatic S-methylation, nonenzymatic oxidation, and/or conversion to thiourate by xanthine oxidase. Azathioprine reacts with sulfhydryl compounds such as glutathione (reported to be by nonenzymatic pathways) which produces a more controlled liberation of mercaptopurine in tissues. Azathioprine is also reported to provide enhanced immunosuppressive activity relative to unmodified 6-MP. In spite of this advance, further improvements have been sought in order to deliver various mercaptan-based therapeutic agents in ways which would be therapeutically superior to that which is currently available. For example, it would be desirable to reduce the number of dosages a patient would require and/or more predictable control the rate of release of the drug from a carrier.

Incorporating a polymer as part of a prodrug system has been suggested to increase the circulating life of some drugs having an available hydroxyl or amine group. See, for example U.S. Pat. No. 6,180,095, the contents of which are incorporated herein by reference. The '095 patent discloses polymer-based double prodrug systems using a benzyl elimination (BE) system for controllably delivering biologically active materials in vivo.

While a number of polymeric prodrug systems are known to the art, including those prepared by linking a polyethylene glycol (PEG) to a drug or other agent of interest, conjugates that directly exploit the thiol function groups of many potentially useful biologically effective substances are not believed to be mentioned. Protected sulfur-linked polyethylene glycols are also known, although these ultimately form polymer-drug conjugates via covalent disulfide bonds (—S—S— bonds) not via covalent thiol bonds (—SH— bonds). See Woghiren et al., 1993, Bioconjugate Chem. 4: 314-318, who linked a 5 kDa PEG to papain enzyme by disulfide linkers.

Thus, there remains a need for improved polymeric prodrug systems for thiol- or mercaptan containing compounds. There is also a need for including benzyl elimination systems as part of such prodrug systems. The present invention addresses these needs.

SUMMARY OF THE INVENTION

In one aspect of the invention, compounds of Formulae (Ia) and (Ib) are provided:

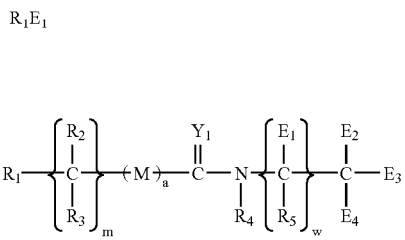

(Ia)

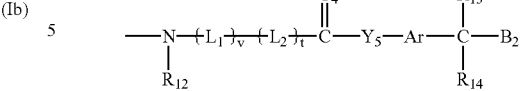

(Ib)

wherein:

$R_1$ is a polymeric residue;

$Y_1$ is O, S or $NR_{10}$;

M is O, S or $NR_{11}$;

(m) is zero or a positive integer, preferably 1 or 2;

(a) is zero or one;

(w) is zero or one;

$E_1$ is

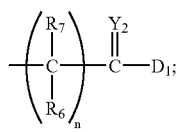

$E_{2-4}$ are independently H, $E_1$ or

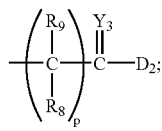

(n) and (p) are independently 0 or a positive integer;

$Y_{2-3}$ are independently O, S or $NR_{15}$;

$R_{2-11}$ and $R_{15}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$D_1$ and $D_2$ are independently OH, (IV)

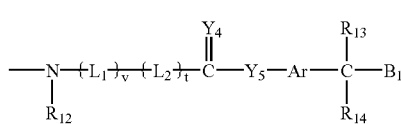

-continued (V)

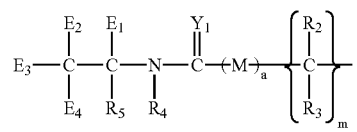

or additional branching groups described below, wherein (v) and (t) are independently 0 or 1;

$L_1$ and $L_2$ are independently selected heterobifunctional linkers;

$Y_{4-5}$ are independently selected from the group consisting of O, S and $NR_{16}$;

$R_{12-14}$ and $R_{16}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroakoxy;

Ar is a moiety which when included in Formula (I) forms a multi-substituted aromatic hydrocarbon or a multi-substituted heterocyclic group; and $B_1$ and $B_2$ are independently selected from the group consisting of leaving groups, OH and residues of sulfhydryl-containing moieties.

In one particularly preferred aspect of the invention, the polymeric residue is also substituted on the distal portion with a moiety of formula (II) below:

(II)

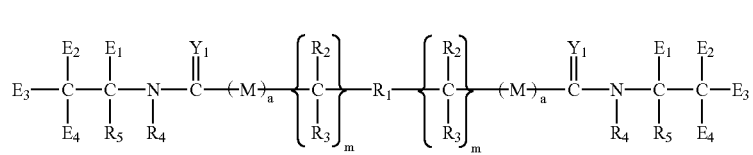

where all variables are as previously defined. Bifunctional compounds are thus formed when the polymeric residue ($R_1$) includes both an alpha and an omega terminal linking group so that two, four or more equivalents of a biologically active agent, drug or protein, designated herein as $B_1$ or $B_2$ can be delivered. An example of such a bifunctional polymer transport form is illustrated below as formula (III):

(III)

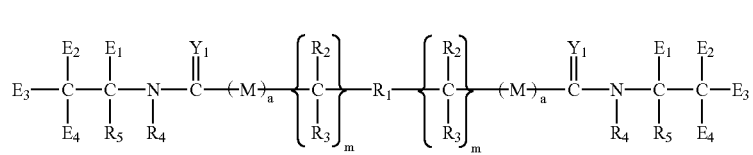

wherein all variables are as described above.

For purposes of the present invention, the term "residue" shall be understood to mean that portion of a biologically active compound which remains after the biologically active compound has undergone a substitution reaction in which the prodrug carrier portion has been attached.

For purposes of the present invention, the term "alkyl" shall be understood to include straight, branched, substituted, e.g. halo-, alkoxy-, and nitro-$C_{1-12}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromophenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo shall be understood to include fluoro, chloro, iodo and bromo.

The term "sufficient amounts" for purposes of the present invention shall mean an amount which achieves a therapeutic effect as such effect is understood by those of ordinary skill in the art.

One of the chief advantages of the compounds of the present invention is that the prodrugs have a higher payload per unit of polymer than previous techniques. The high payload polymeric conjugates of the present invention are thus unique payload systems which can contain up to four or a greater number of molecules of a drug. It is generally preferred that the polymeric first releases the benzyl elimination (BE) based prodrug intermediate by hydrolysis and then the resultant intermediate or "second prodrug" moiety undergoes a 1,4- or 1,6-aryl (e.g., benzyl) elimination reaction to regenerate, for example, a moiety which is either a biologically active compound or a composition comprising a further prodrug.

Methods of making and using the compounds and conjugates described herein are also provided.

DETAILED DESCRIPTION OF THE INVENTION

A. Formulae (Ia) and (Ib)

Figure 1:
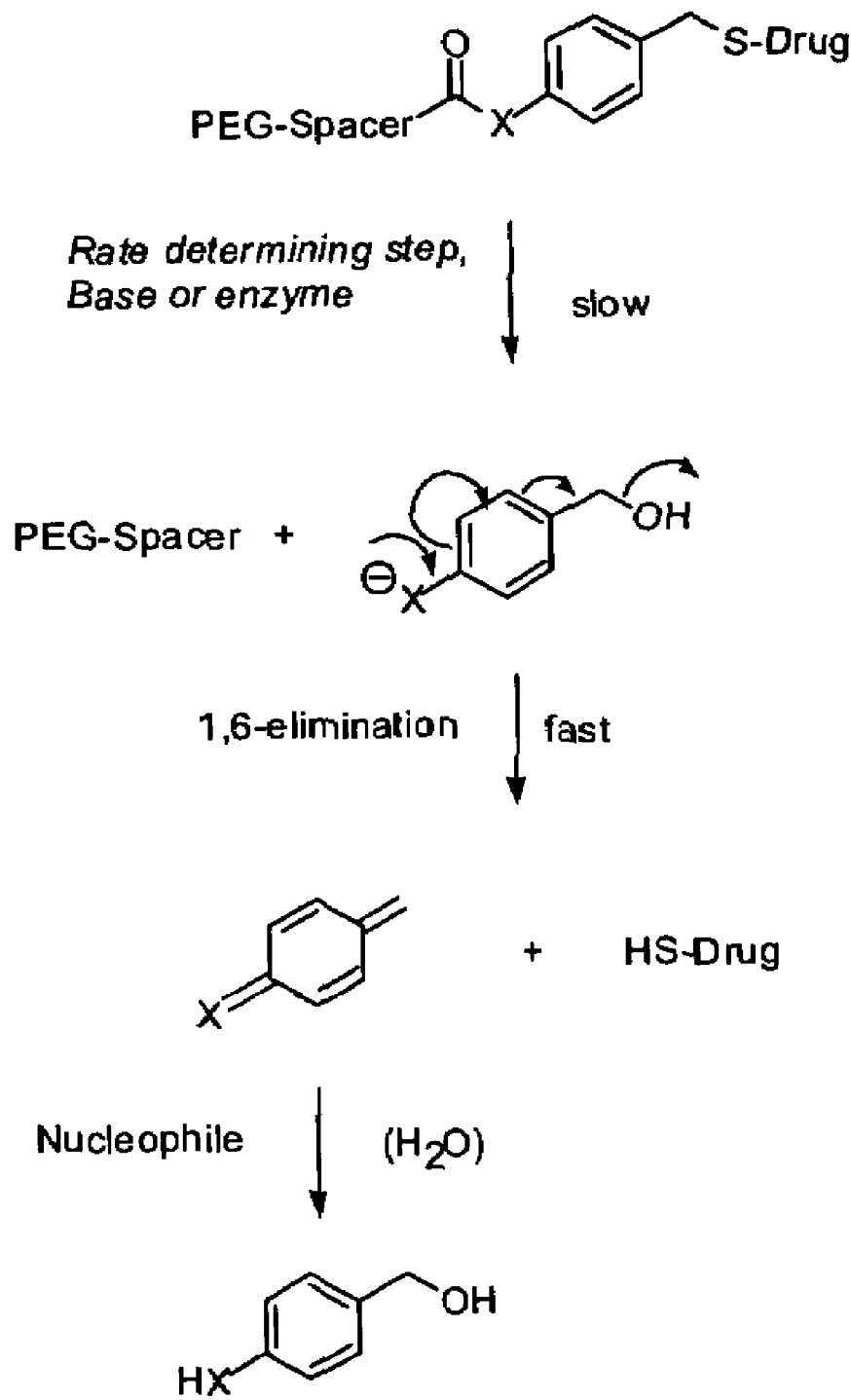
FIG. 1 schematically illustrates the releasing mechanism prodrugs prepared in accordance with the present invention.
Figure 2:
FIG. 2 illustrates the definitions for structural abbreviations used in FIGS. 3-6c.
Figure 2:
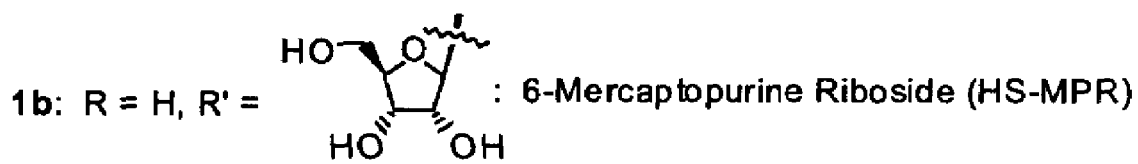
Figure 2:
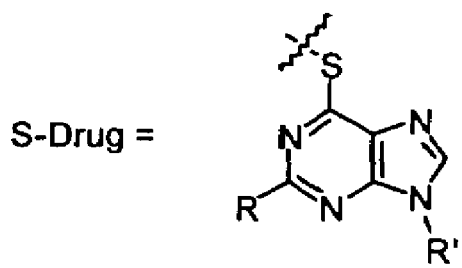
Figure 2:
Figure 3A:
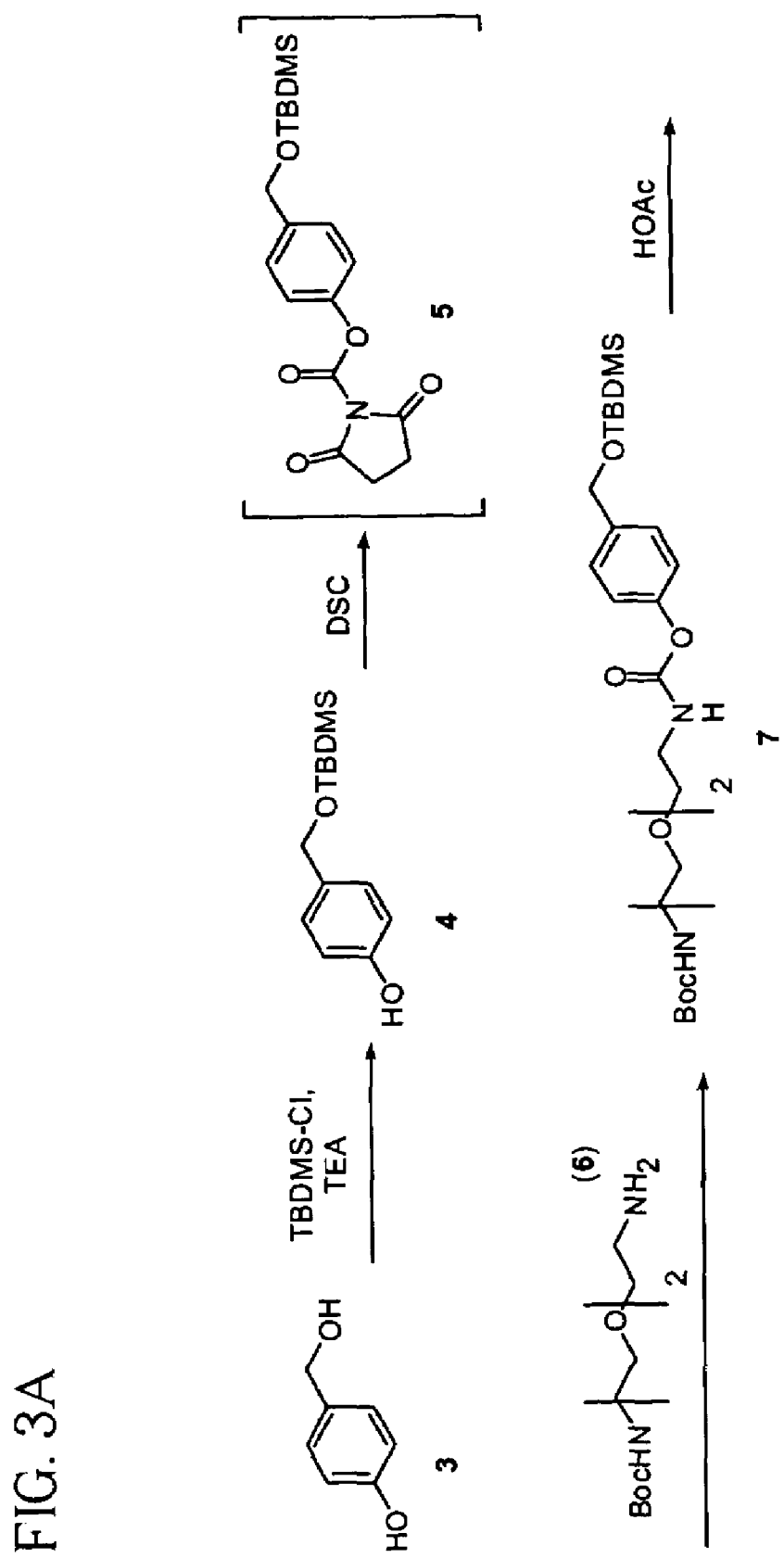
FIGS. 3-6c illustrate the synthesis of various inventive compounds described in the Examples.
Figure 3B:
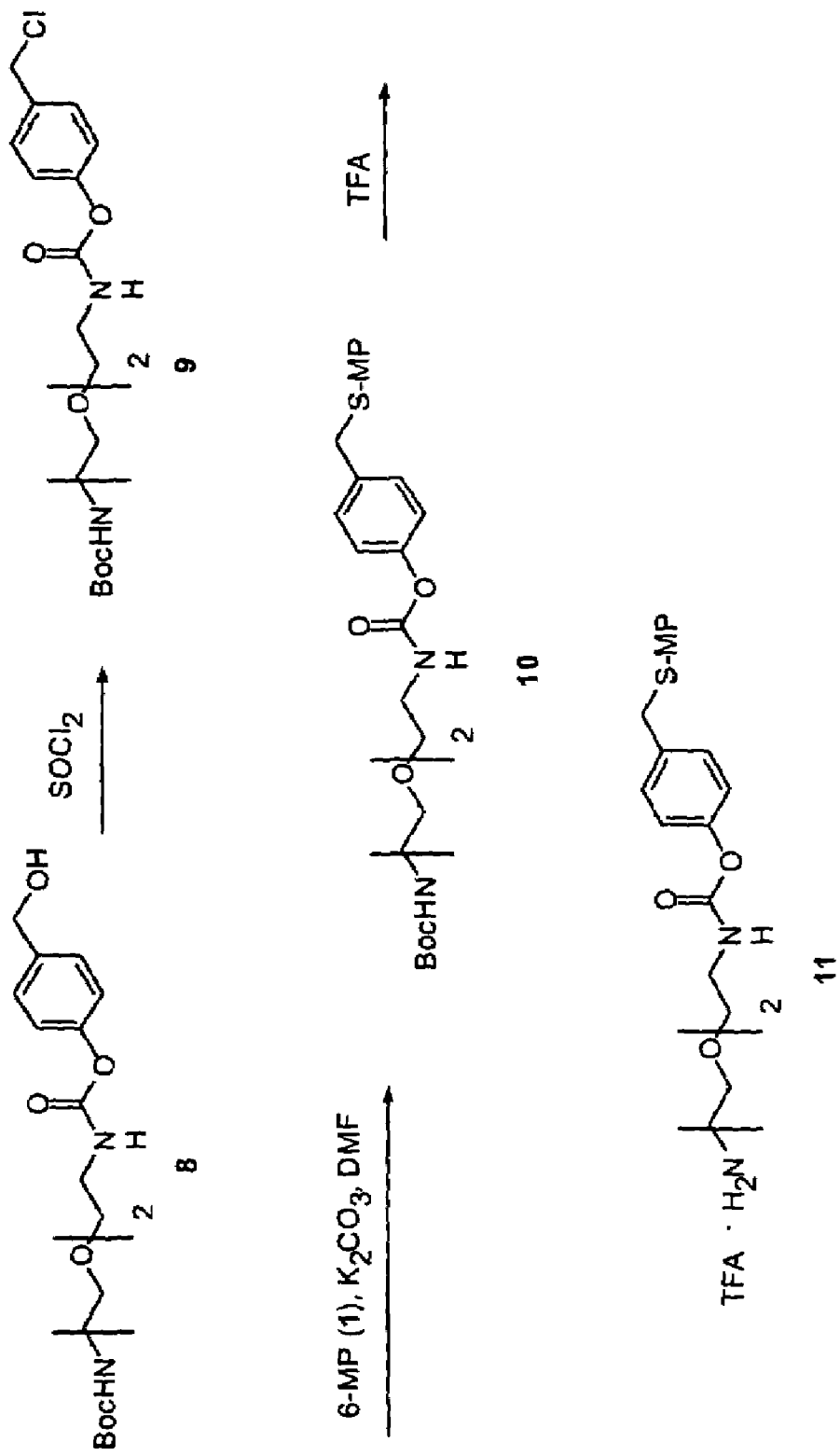
Figure 4A:
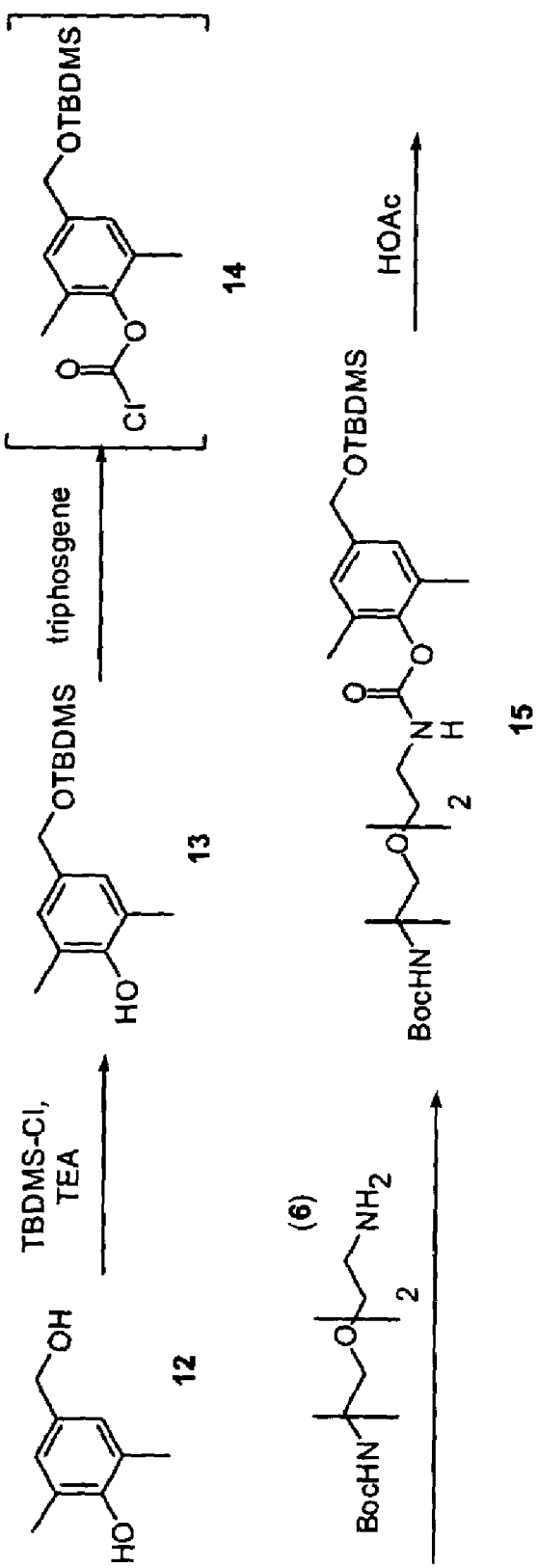
Figure 4B:
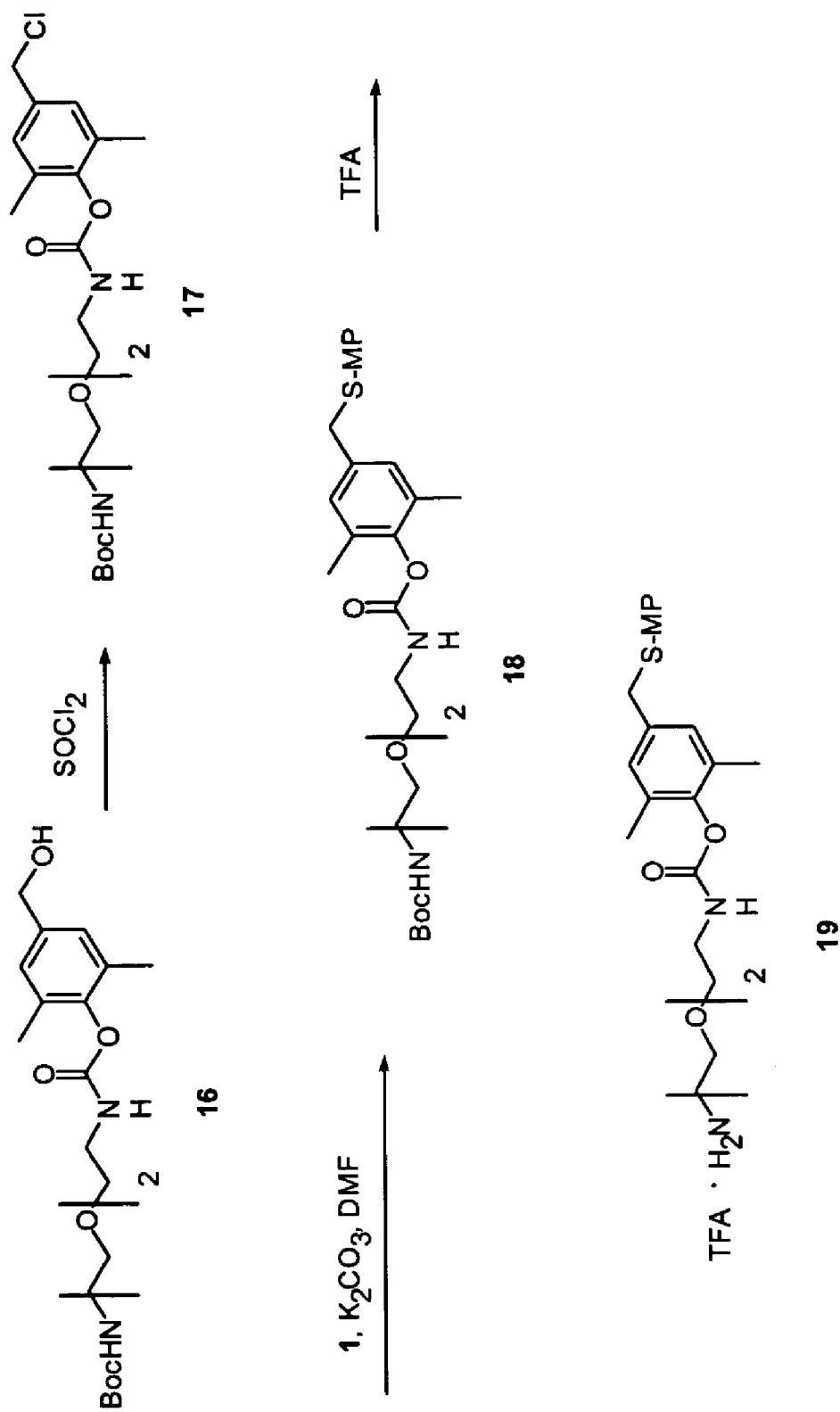
Figure 5A:
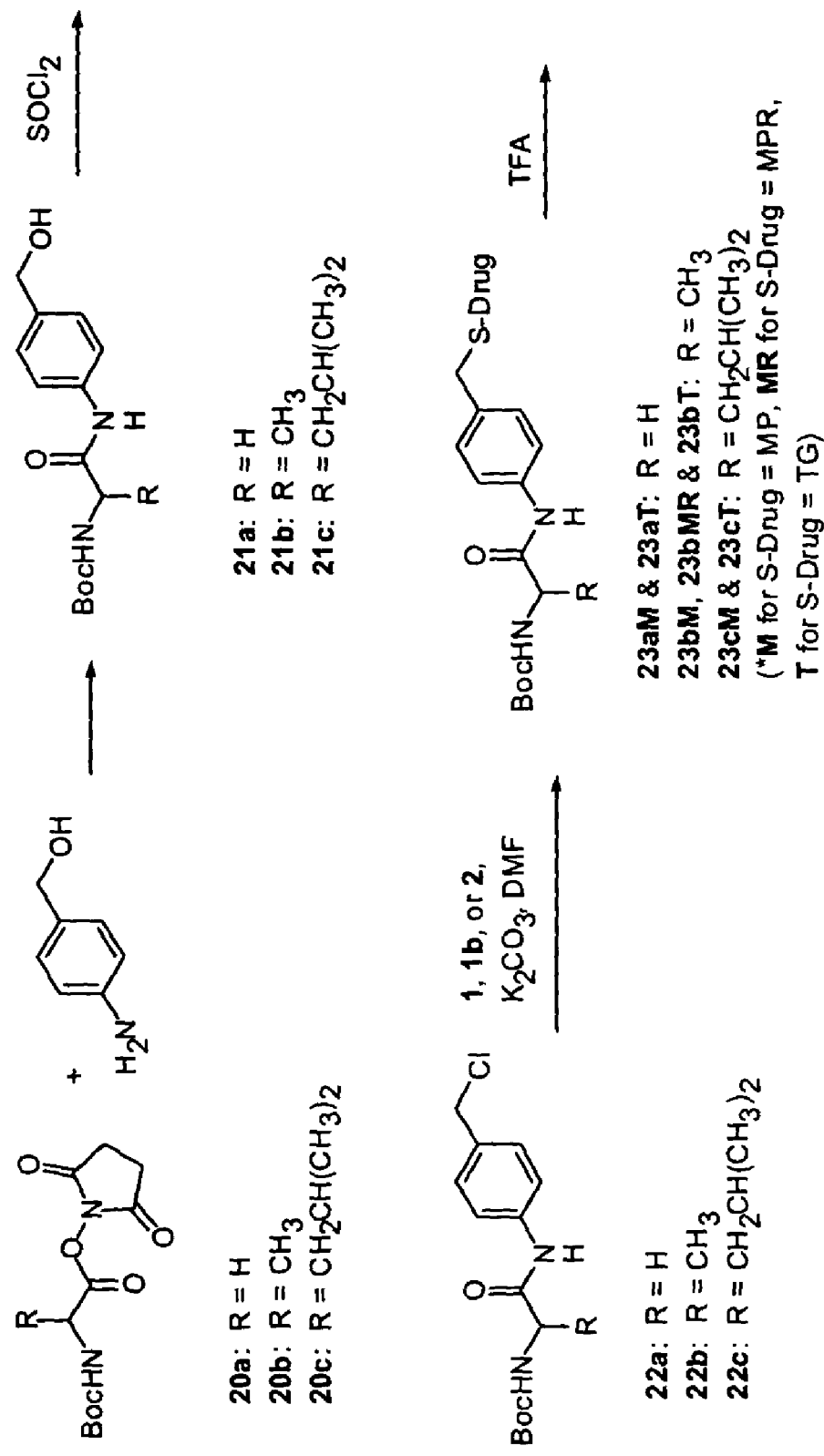
Figure 5B:
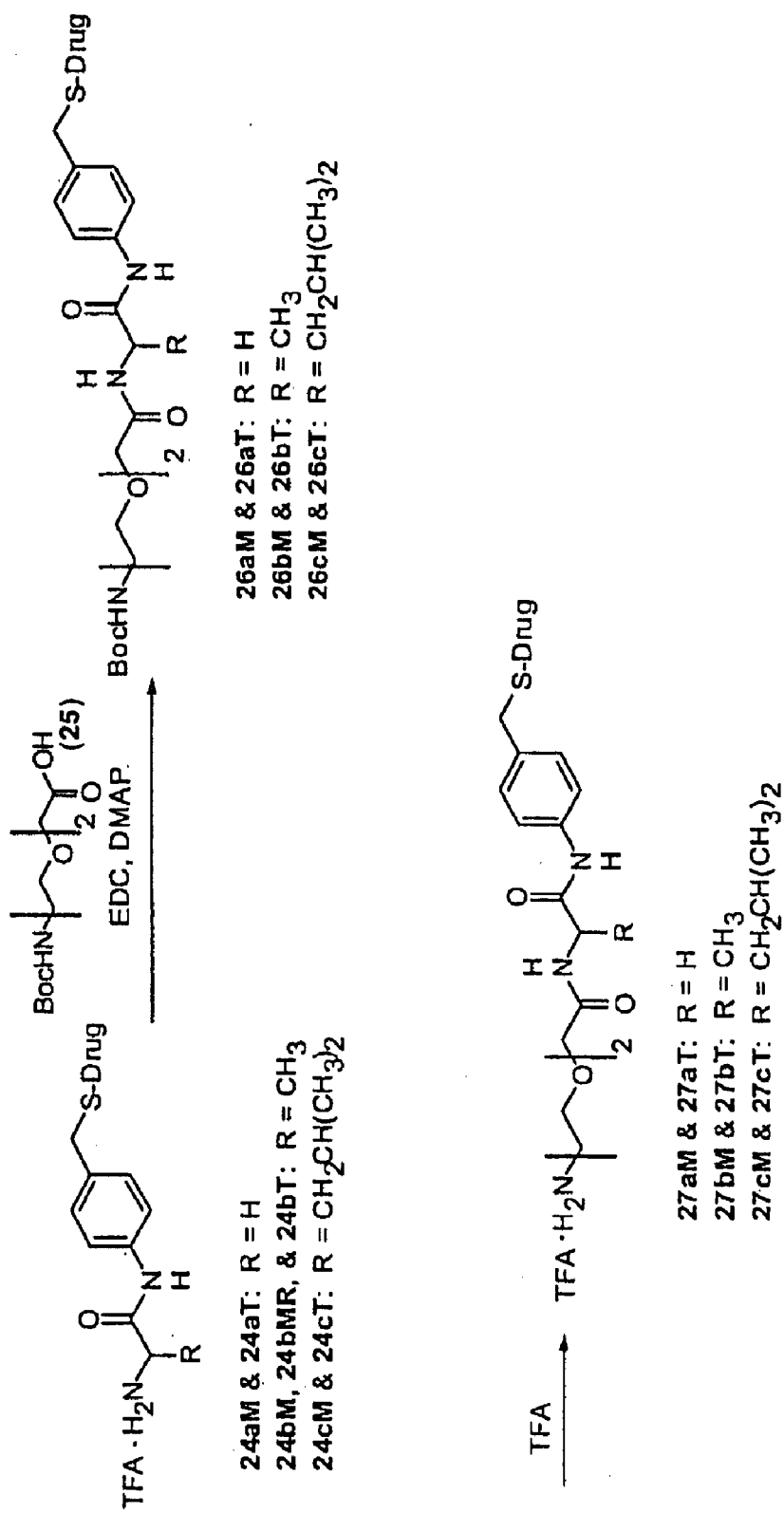
Figure 6A:
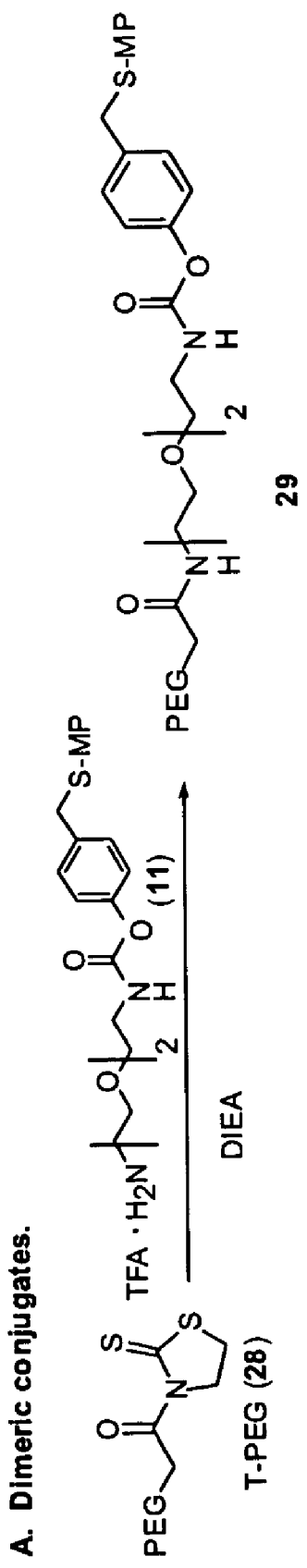
Figure 6B:
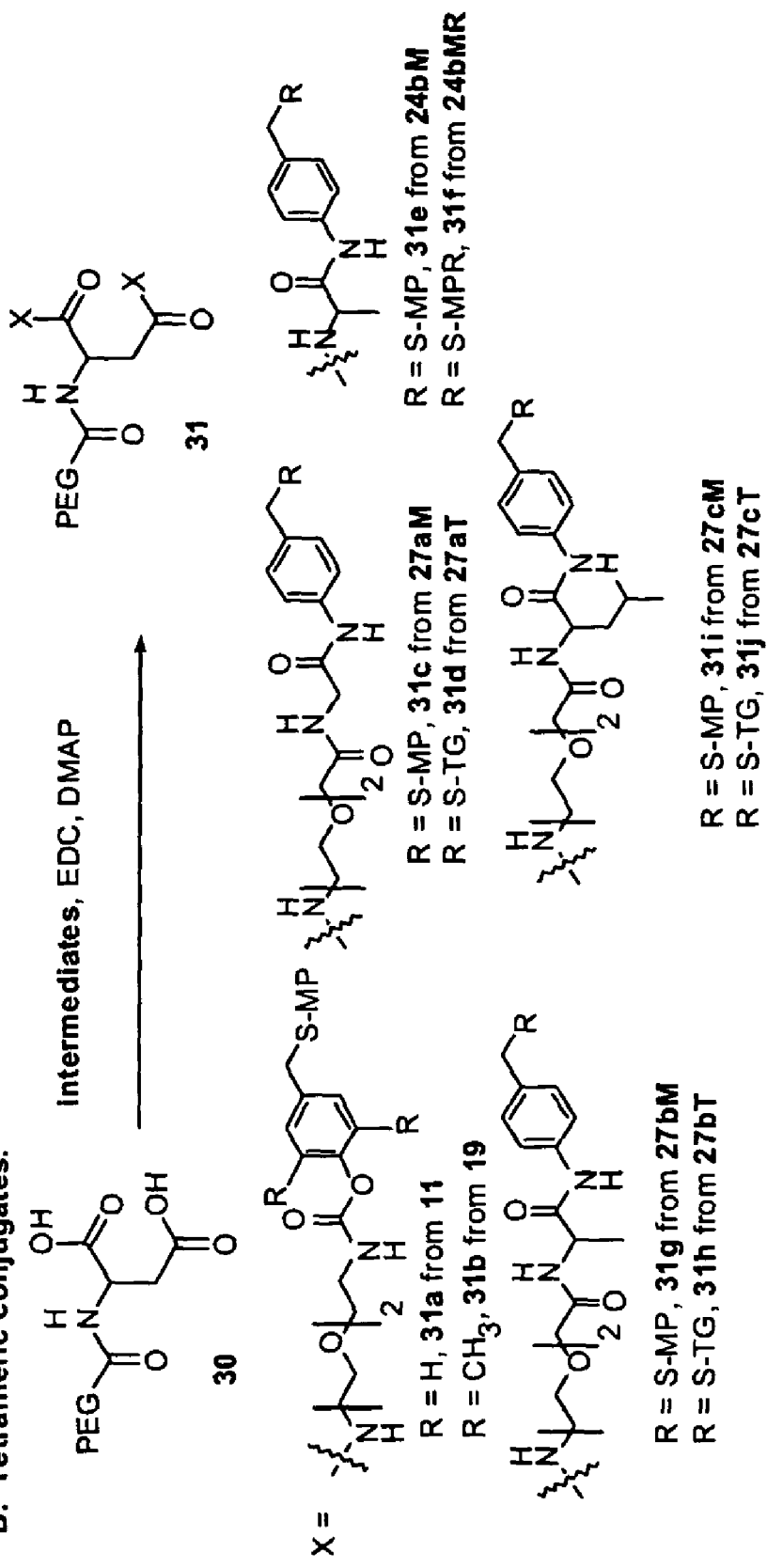
Figure 6C:
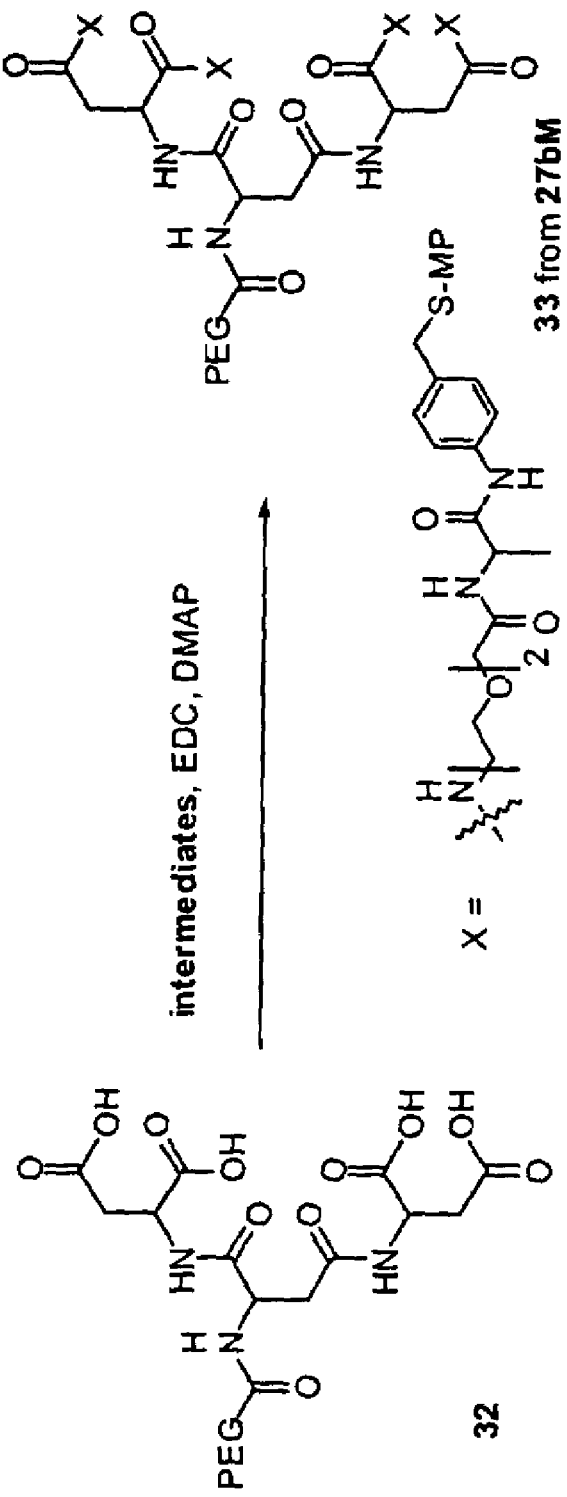

In some preferred embodiments of the invention, there are provided compounds of the formula:

 (Ia)

and

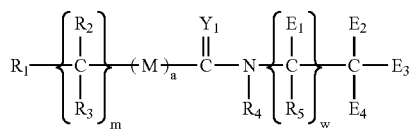 (Ib)

wherein:
$R_1$ is a polymeric residue;
$Y_1$ is O, S or $NR_{10}$;
M is O, S or $NR_{11}$;
$E_1$ is

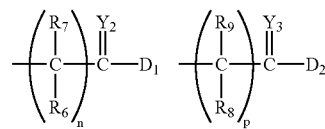

$E_{2-4}$ is are independently H, $E_1$ or
(a) is zero or one;
(m) is zero or a positive integer;
(w) is zero or one;
(n) and (p) are independently 0 or a positive integer;
$Y_{2-3}$ are independently O, S or $NR_{12}$;
$R_{2-12}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
$D_1$ and $D_2$ are independently OH,

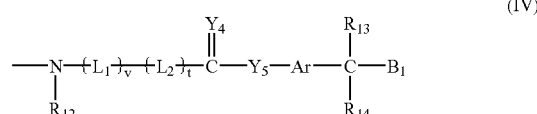 (IV)

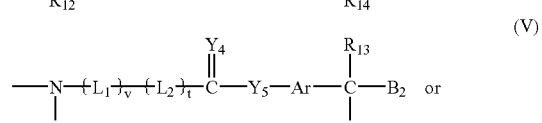 (V)

 (VI)

wherein:
$R'_4$ and $R'_5$ are the selected from the same group which defines $R_4$ and $E_{35-38}$ are selected from the same group which defines $E_{1-4}$ above, except that within the definition, $D_1$ and $D_2$ are changed to $D'_1$ and $D'_2$ which are defined below. Within this embodiment, $D'_1$ and $D'_2$ can be independently OH, a moiety of formula (IV), (V), or

 (VII)

wherein $R''_4$ and $R''_5$ are independently selected from the same group which defines $R_4$ and $E_{45-48}$ are selected from the same group which defines $E_{1-4}$, except that within the definition $D_1$ and $D_2$ are changed to $D''_1$ and $D''_2$ and $D''_1$ and $D''_2$ can be independently OH, formula (IV) or formula (V). As can be appreciated from the above, when the terminal branching is taken to its fullest extent with a bifunctional polymer $R_1$, up to sixteen (16) equivalents of drug can be loaded onto the polymeric platform.

The remaining variables of formulas (IV) and (V) are defined as:

(v) and (t) are independently 0 or 1;

$L_1$ and $L_2$ are independently selected heterobifunctional linkers;

$Y_{4-5}$ are independently selected from the group consisting of O, S and $NR_{16}$;

$R_{12-14}$ and $R_{16}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is a moiety which when included in Formula (I) forms a multi-substituted aromatic hydrocarbon or a multi-substituted heterocyclic group; and $B_1$ and $B_2$ are preferably independently selected from among OH and residues of sulfhydryl-containing moieties. In alternative embodiments, $B_{1-2}$ can be independently selected leaving groups.

In those aspects of this embodiment where bis-substituted polymeric residues are desired, some preferred polymeric transport systems of the invention are shown below as formulae

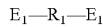  (IIIa)

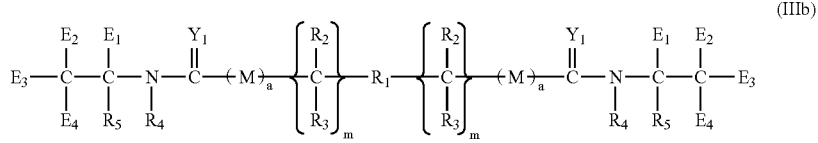  (IIIb)

wherein all variables are as previously described.

The multi-loading polymer transport system of the present invention is based in large part on the polymeric residue designated herein as $R_1$. Optionally, $R_1$ includes a capping group A. The polymer capping group A includes, for example, moieties such as hydrogen, $NH_2$, OH, $CO_2H$, $C_{1-6}$ alkyl moieties, and compounds of formula (IIa) and (IIb) shown below, which forms bis-systems:

  (IIa)

or

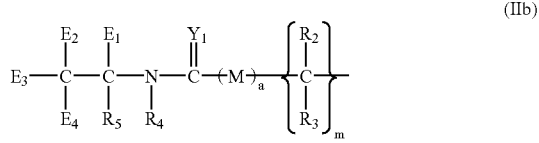  (IIb)

wherein all variables are as previously described. It will be understood and appreciated that the multiple terminal branching described above applies equally in the bis-systems as well and that the biologically active moieties on the terminals can be the same SH-containing moiety or different.

With regard to the other variables which comprise the formulae of the present invention, the following are preferred:

$Y_{1-4}$ are each oxygen;

the R variables other than $R_1$, e.g., $R_2$-$R_{11}$, etc. are each preferably hydrogen or lower, e.g. $C_{1-6}$ alkyl;

(m) is 1 or 2;

(v) is zero or 1;

(t) is 1;

$L_1$ is $-(CH_2CH_2O)_2-$; and $L_2$ is one of $-CH_2-$, $-CH(CH_3)-$, $CH[CH_2CH(CH_3)_2]-$, $-CH_2C(O)NHCH(CH_3)-$, $-(CH_2)_2-$, $-CH_2C(O)NHCH_2-$, $CHC(O)NHCH[CH_2CH(CH_3)_2]$, $-(CH_2)_2-NH-$ or $-(CH_2)_2-NH-C(O)(CH_2)_2NH-$.

B. Description of the Ar Moiety

Referring to Formula (I), it can be seen that the Ar is a moiety, which when included in Formula (I), forms a multi-substituted aromatic hydrocarbon or a multi-substituted heterocyclic group. A key feature is that the Ar moiety is aromatic in nature. Generally, to be aromatic, the π electrons must be shared within a "cloud" both above and below the plane of a cyclic molecule. Furthermore, the number of π electrons must satisfy the Hückle rule (4n+2). Those of ordinary skill will realize that a myriad of moieties will satisfy the aromatic requirement of the moiety and thus are suitable for use herein. Some particularly preferred aromatic groups include:

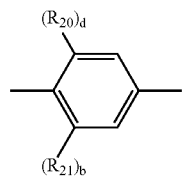

where $R_{20-21}$ are individually selected from the same group which defines $R_2$ and (b) and (d) are independently zero or one.

Other preferred aromatic hydrocarbon moieties include, without limitation:

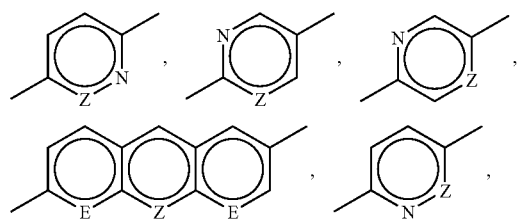

-continued

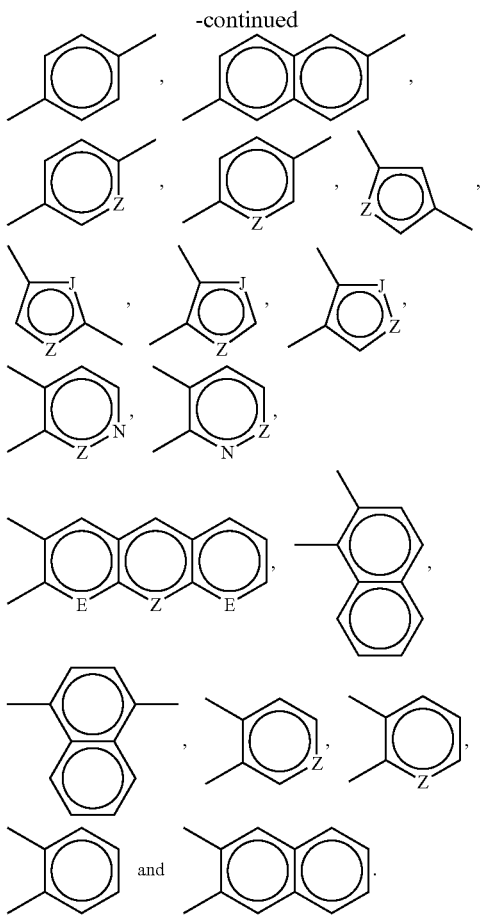

In the above-listed aromatic moieties, J is O, S, or N—$R_{22}$, E and Z are independently C—$R_{23}$ or N—$R_{24}$; and $R_{22-24}$ are independently selected from the same group as that which defines $R_2$ in Formula (I) e.g., hydrogen, $C_{1-6}$ alkyls, etc. Isomers of the five and six-membered rings are also contemplated as well as benzo- and dibenzo-systems and their related congeners. It will also be appreciated by the artisan of ordinary skill that the aromatic rings can optionally be substituted with heteroatoms such as O, S, $NR_{22}$, etc. so long as Hückel's rule is obeyed. Furthermore, aromatic or heterocyclic structures may optionally be substituted with halogen(s) and/or side chains as those terms are commonly understood in the art. However, all structures suitable for Ar moieties of the present invention are capable of allowing the $Y_5$ and $C(R_{13})(R_{14})$ moieties to be in a para or an ortho arrangement with the same plane.

C. Drug Generation Via Hydrolysis of the Prodrug

The prodrug compounds of the present invention are designed so that the $t_{1/2}$ of hydrolysis is <$t_{1/2}$ elimination in plasma.

The linkages included in the compounds have hydrolysis rates in the plasma of the mammal being treated which is short enough to allow sufficient amounts of the parent compounds, i.e. the amino- or hydroxyl-containing bioactive compound, to be released prior to elimination. Some preferred compounds of the present invention have a $t_{1/2}$ for hydrolysis in plasma ranging from about 5 minutes to about 12 hours. Preferably, the compositions have a plasma $t_{1/2}$ hydrolysis ranging from about 0.5 to about 8 hours and most preferably from about 1 to about 6 hours.

D. Substantially Non-Antigenic Polymers

As stated above, $R_1$ is a polymeric residue which is preferably substantially non-antigenic. In preferred aspects of the invention, $R_1$ further includes the previously mentioned capping group A which allows the bis system to be formed. Suitable examples of such polymers include polyalkylene oxides such as polyethylene glycols. The general formula for PEG and its derivatives is,

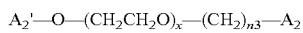

where (x) represents the degree of polymerization (i.e. from about 10 to about 2,300) or number of repeating units in the polymer chain and is dependent on the molecular weight of the polymer, (n3) is zero or a positive integer, ($A_2$) is a capping group as defined herein, i.e. amino, carboxy, halo, $C_{1-6}$ alkyl or other activating group and ($A'_2$) is the same as ($A_2$) or another ($A_2$) moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997-1998". The disclosure of each of the foregoing is incorporated herein by reference. It will be understood that the water-soluble polymer can be functionalized for attachment to the linkage via M, herein. As an example, the PEG portion of the inventive compositions can be one of the following non-limiting compounds:

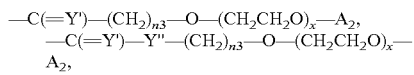

and

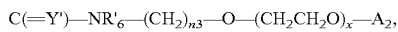

where Y' and Y" are independently O or S and $A_2$, (n3) and (x) are as defined above and $R'_6$ is selected from the same group which defines $R_6$. See also commonly-assigned U.S. patent application Ser. No. 09/293,624, filed Apr. 16, 1999 and U.S. Pat. No. 6,153,655. The contents of each are incorporated herein by reference.

In many aspects of the present invention, bis-activated polyethylene glycols are preferred when di- or more substituted polymer conjugates are desired. Alternatively, polyethylene glycols (PEGs), mono-activated, $C_{1-4}$ alkyl-terminated PAO's such as mono-methyl-terminated polyethylene glycols (mPEG's) are preferred when mono-substituted polymers are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in number average molecular weight, polymers ranging from about 2,000 to about 100,000 are usually selected for the purposes of the present invention. Molecular weights of from about 5,000 to about 50,000 are preferred and 20,000 to about 40,000 are particularly preferred. The number average molecular weight of the polymer selected for inclusion in the prodrug must be sufficient so as to provide sufficient circulation of the prodrug before hydrolysis of the linker. Within the ranges provided above, polymers having molecular weight ranges of at least 20,000 are preferred for chemotherapeutic and organic moieties.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bifunctional linking groups are also contemplated.

E. Prodrug Candidates

As shown in Formulae (I) and (II), $B_1$ and $B_2$ are independently selected residues of SH-containing moieties. A non-limiting list of suitable SH-containing moieties include biologically active materials such as 6-mercaptopurine, 6-thioguanine or others as illustrated below:

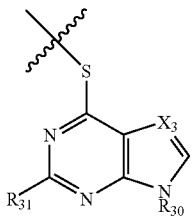

wherein $R_{30}$ is one of H, a $C_{1-6}$ alkyl, alkoxy, or a carbohydrate of the formula:

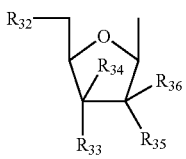

wherein $R_{32-36}$ are independently selected from alkoxy, e.g. $OR_{37}$ or, in the alternative, H, OH, $N_3$, $NHR_{38}$, $NO_2$ or CN, fluoro, chloro, bromo, iodo, where $R_{37-38}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, halo, substituted aryls, aralkyls, $C_{1-6}$ heteroalkyls, substituted $C_{1-6}$ heteroalkyls; and are preferably H or a $C_{1-4}$ alkyl;

$R_{31}$ is H or $NH_2$; and $X_3$ is CH or N.

One preferred $R_{30}$ moiety is:

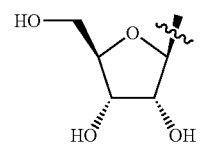

Other suitable candidates for inclusion in the prodrug systems described herein include biologically active compounds such as chemotherapeutic moieties containing a modifiable SH— group and/or polypeptides or enzymes, etc. containing modifiable cysteine residues. A non-limiting list of suitable biologically active compounds include 1-β-D-ribofuranosyl-thiopurine, 1-β-D-arabinofuranosyl-thiopurine, penicillamine, 2-thiouracil, captopril, tiopronin, vasopressin, deaminooxytocin, thiopental sodium, etc.

The only limitations on the types of sulfhydryl-containing molecules suitable for inclusion herein is that there is available at least one SH containing position which can react and link with a carrier portion and that there is not substantial loss of bioactivity after the prodrug system releases and regenerates the parent compound.

It is noted that parent compounds suitable for incorporation into the prodrug compositions of the invention, may themselves be substances/compounds which are not active after hydrolytic release of an intermediate from the linked polymeric composition, but which will become active after undergoing a further chemical process/reaction. For example, an anticancer drug that is delivered to the bloodstream by the double prodrug transport system, may remain inactive until entering a cancer or tumor cell, whereupon it is activated by the cancer or tumor cell chemistry, e.g., by an enzymatic reaction unique to that cell.

1. Leaving Groups

In those aspects where $B_1$ or $B_2$ is a leaving group, suitable leaving groups include, without limitations, moieties such as N-hydroxybenzotriazolyl, halogen, N-hydroxyphthalimidyl, p-nitrophenoxy, imidazolyl, N-hydroxysuccinimidyl; thiazolidinyl thione, or other good leaving groups as will be apparent to those of ordinary skill. The synthesis reactions used and described herein will be understood by those of ordinary skill without undue experimentation.

For example, an acylated intermediate of compound (I) can be reacted with a reactant such as 4-nitrophenyl chloroformate, disuccinimidyl carbonate (DSC), carbonyldiimidazole, thiazolidine thione, etc. to provide the desired activated derivative.

The selective acylation of the phenolic or anilinic portion of the p-hydroxybenzyl alcohol or the p-aminobenzyl alcohol and the o-hydroxbenzyl alcohol or the o-aminobenzyl alcohol can be carried out with, for example, thiazolidine thione activated polymers, succinimidyl carbonate activated polymers, carboxylic acid activated polymers, blocked amino acid derivatives. Once in place, the "activated" form of the PEG prodrug (or blocked prodrug) is ready for conjugation with a sulfhydryl-containing compound.

F. Synthesis of the Polymeric Prodrug Transport System

Synthesis of representative polymer prodrugs is set forth in the Examples. Generally, however, in one preferred method of preparing the prodrug transport systems, the polymer residue is first attached to the branching groups. Separately, the biologically active moiety or drug, e.g. Drug-SH ($B_1$ or $B_2$ of formula I) is attached to the BE component which may also include a bifunctional spacer thereon at point of attachment to the polymer. Next, the polymeric residue containing the terminal branches is reacted with the drug-BE portion under conditions sufficient to form the final product.

Attachment of the bifunctional spacer containing the BE-Drug component to the polymer portion is preferably carried out in the presence of a coupling agent. A non-limiting list of suitable coupling agents include 1,3-diisopropylcarbodiimide (DIPC), any suitable dialkyl carbodiimides, 2-halo-1-alkyl-pyridinium halides, (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as methylene chloride, chloroform, DMF or mixtures thereof. The reaction also preferably is conducted in the presence of a base, such as dimethylaminopyridine, diisopropylethylamine, pyridine, triethylamine, etc. to neutralize any acids generated and at a temperature from 0° C. up to about 22° C. (room temperature).

More particularly, one method of preparing a polymeric transport system includes reacting a compound of the formula (VIII):

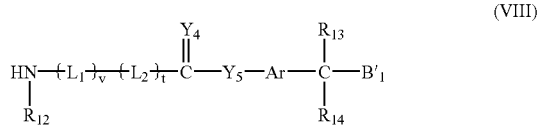

(VIII)

wherein (v) and (t) are independently 0 or 1;

$L_1$ and $L_2$ are independently selected heterobifunctional linkers;

$Y_{4-5}$ are independently selected from the group consisting of O, S and $NR_{16}$;

$R_{12-14}$ and $R_{16}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is a moiety which when included in Formula (I) forms a multisubstituted aromatic hydrocarbon or a multi-substituted heterocyclic group; and $B'_1$ is a residue of a sulfhydryl-containing moiety;

with a compound of the formula (IX):

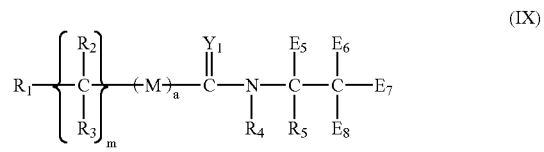

(IX)

wherein $E_5$ is

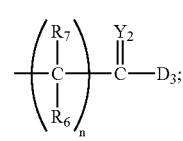

$E_{6-8}$ are independently H, $E_5$ or

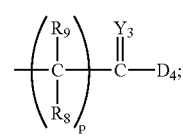

wherein $D_3$ and $D_4$ are independently OH or a leaving group which is capable of reacting with an unprotected amine or

(X)

where $R'_4$ and $R'_5$ are the selected from the same group which defines $R_4$ and $E_{15-18}$ are selected from the same group which defines $E_{5-8}$, except that $D_3$ and $D_4$ are changed to $D'_3$ and $D'_4$ which are defined below. Within this embodiment, $D'_3$ and $D'_4$ can be independently OH, a moiety of formula (IV) or (V), or

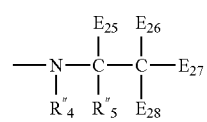

(XI)

wherein $R''_4$ and $R''_5$ are independently selected from the same group which defines $R_4$ and $E_{25-28}$ are selected from the same group which defines $E_{5-8}$, except that $D_3$ and $D_4$ are changed to $D''_3$ and $D''_4$ which are defined as being independently OH or a leaving group which is capable of reacting with an unprotected amine. Such synthetic techniques allow up to sixteen (16) equivalents of carboxylic acid or activated carboxylic acid, for example, to be attached. As shown in the preferred structures herein, PEG residues with terminally branched multi-acids are preferred aspects of the invention.

Returning to formula (IX), $R_1$ is a polymeric residue; $Y_1$ is O, S or $NR_{10}$; M is O, S or $NR_{11}$; (m), (n) and (p) are independently 0 or a positive integer; $Y_{2-3}$ are independently O, S or $NR_{15}$; and $R_{2-9}$ and $R_{15}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy.

Regardless of the synthesis selected, some of the preferred compounds which result from the synthesis techniques described herein include:

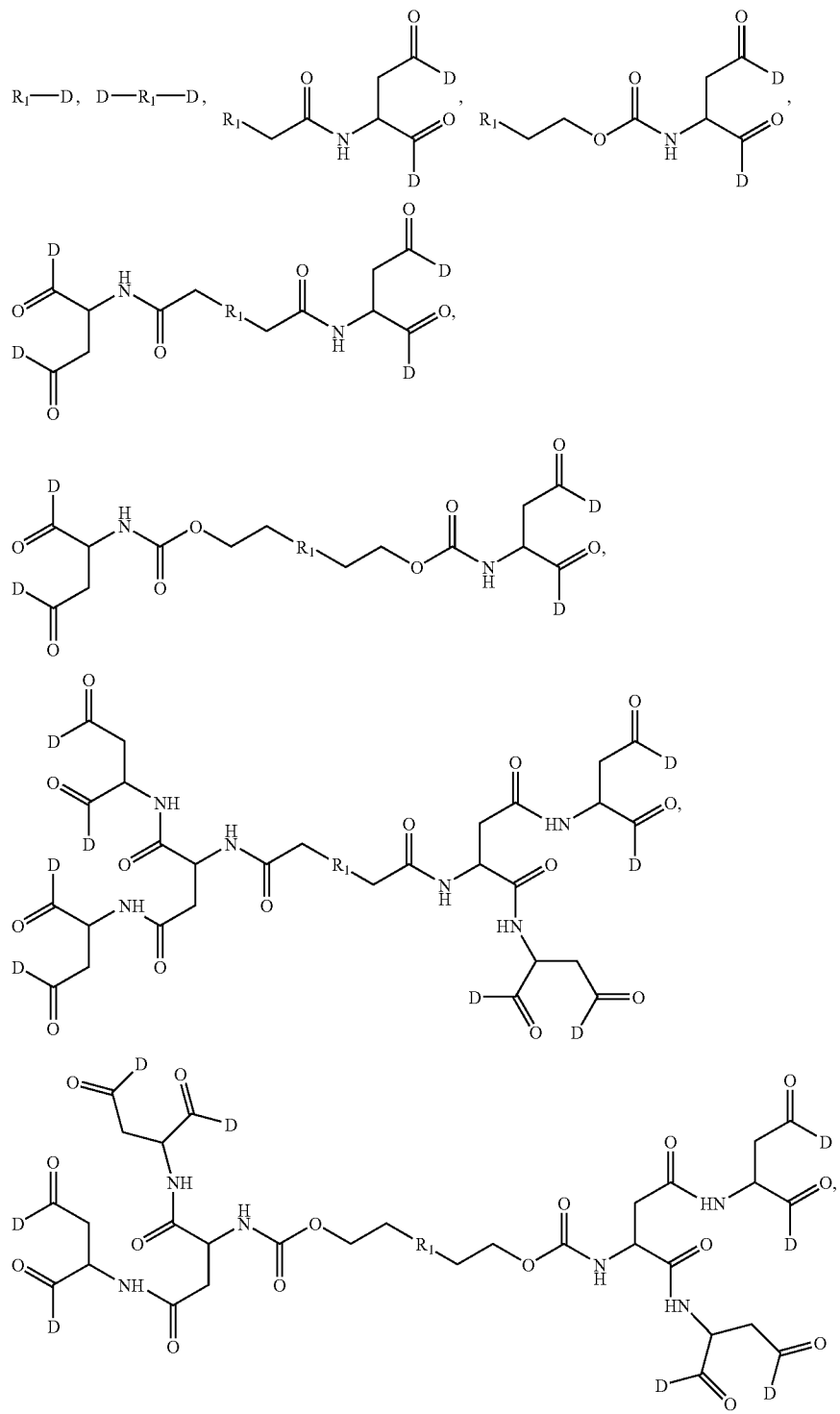

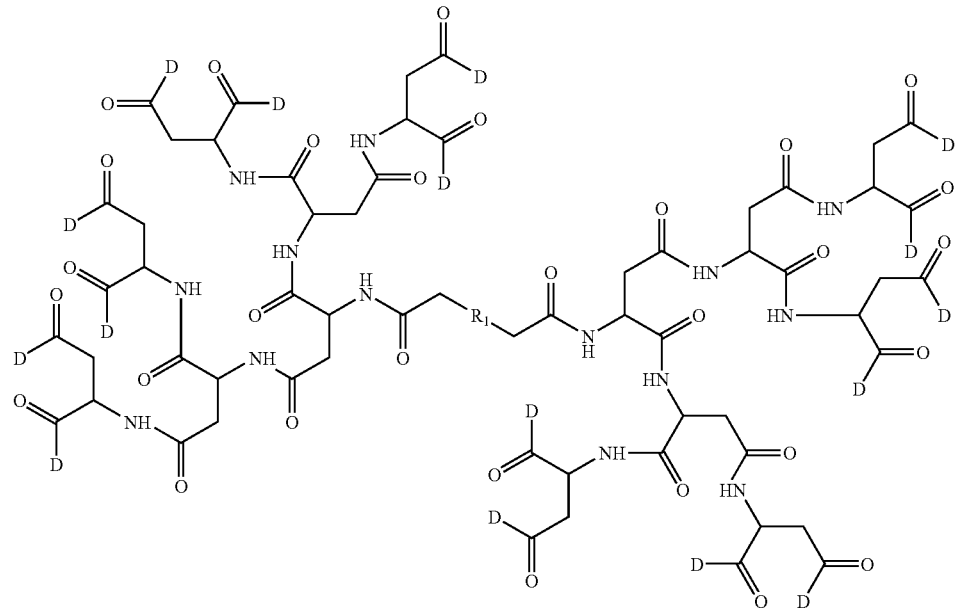
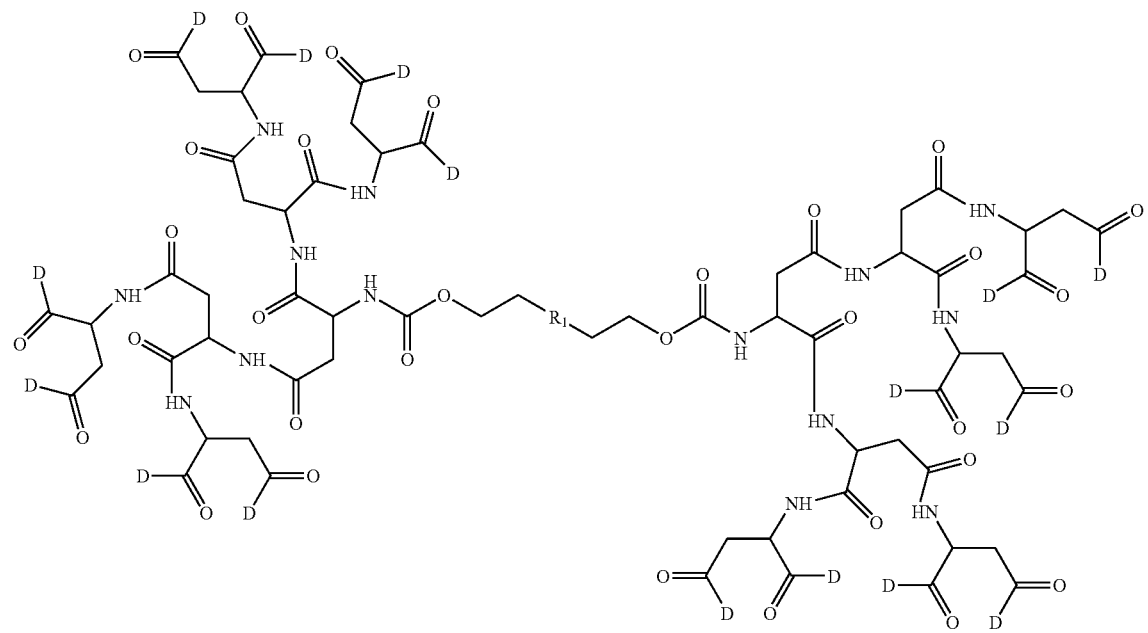
wherein $R_1$ is a PEG residue and D is OH, formula (IV) or (V). Preferably, D is
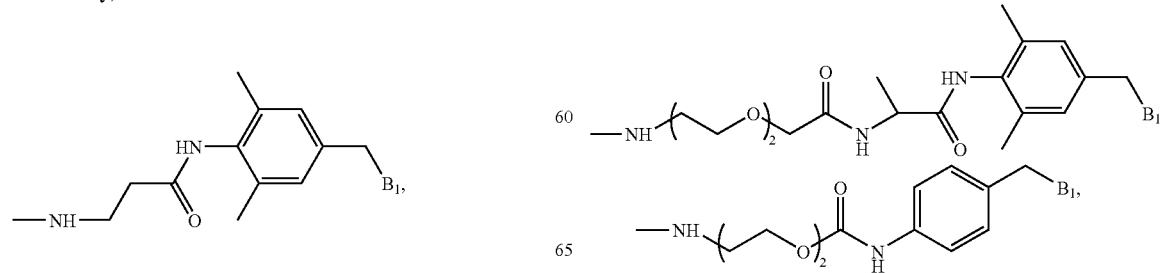

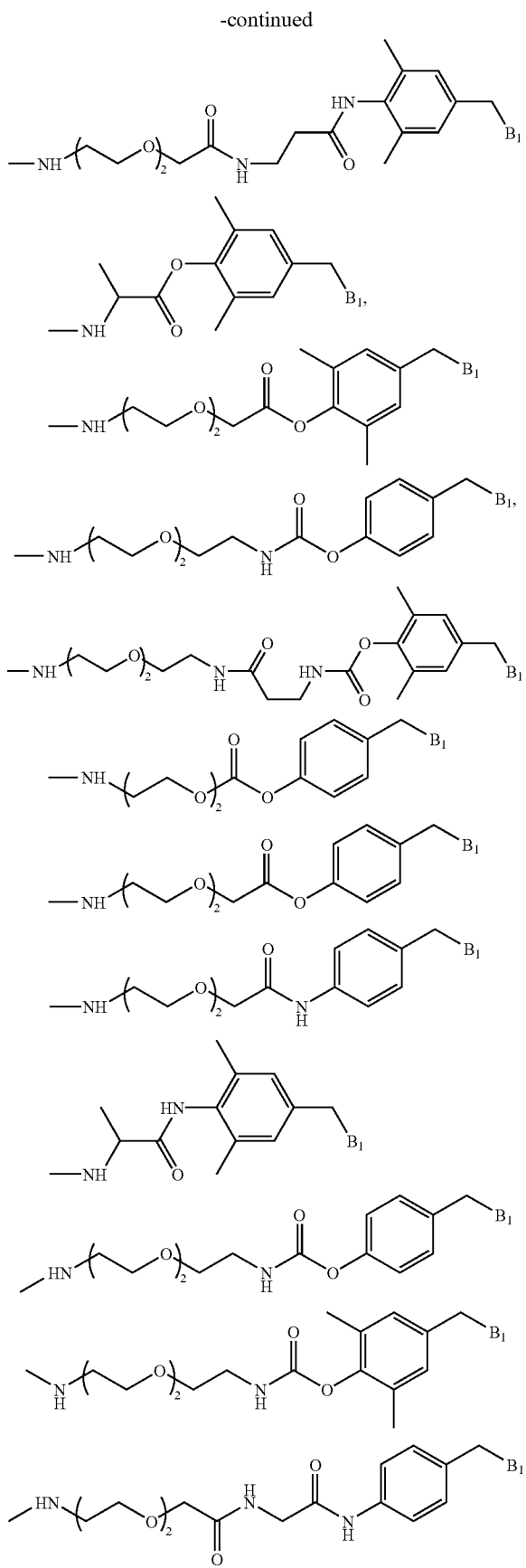

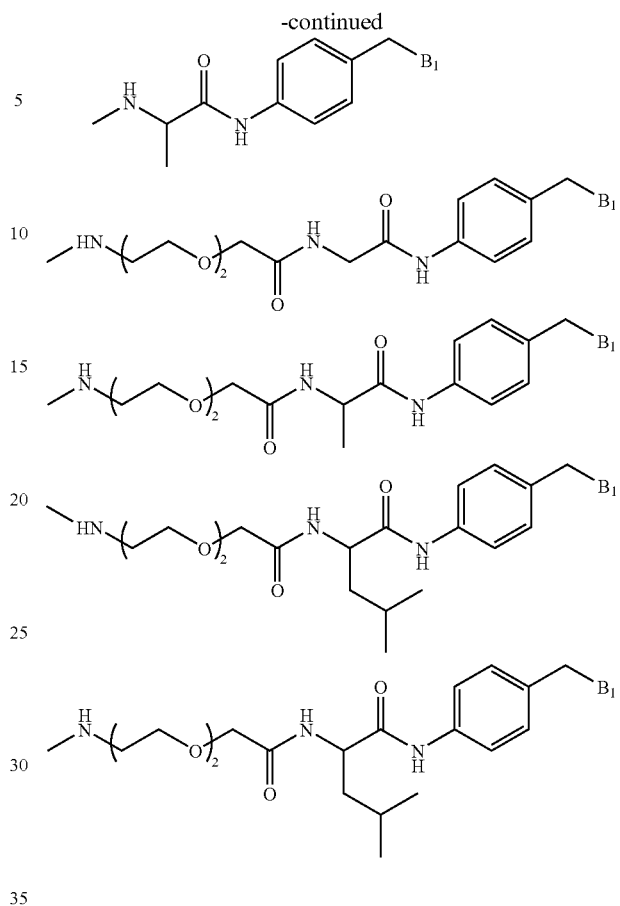

where $B_1$ is a residue of a sulfhydryl-containing drug.

G. In Vivo Diagnostics

A further aspect of the invention provides the conjugates of the invention optionally prepared with a diagnostic tag linked to the transport enhancer described above, wherein the tag is selected for diagnostic or imaging purposes. Thus, a suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In a still further aspect of the invention, the inventive tagged conjugates are readily prepared, by art-known methods, with any suitable label, including, e.g., radioisotope labels. Simply by way of example, these include [131]Iodine, [125]Iodine, [99m]Technetium and/or [111]Indium to produce radioimmunoscintigraphic agents for selective uptake into tumor cells, in vivo. For instance, there are a number of art-known methods of linking peptide to Tc-99m, including, simply by way of example, those shown by U.S. Pat. Nos. 5,328,679; 5,888,474; 5,997,844; and 5,997,845, incorporated by reference herein.

Broadly, for anatomical localization of tumor tissue in a patient, the conjugate tag is administered to a patient or animal suspected of having a tumor. After sufficient time to allow the labeled immunoglobulin to localize at the tumor site(s), the signal generated by the label is detected, for instance, visually, by X-ray radiography, computerized transaxial tomography, MRI, by instrumental detection of a luminescent tag, by a photo scanning device such as a gamma camera, or any other method or instrument appropriate for the nature of the selected tag.

The detected signal is then converted to an image or anatomical and/or physiological determination of the tumor site. The image makes it possible to locate the tumor in vivo and to devise an appropriate therapeutic strategy. In those embodiments where the tagged moiety is itself a therapeutic agents, the detected signal provides evidence of anatomical localization during treatment, providing a baseline for follow-up diagnostic and therapeutic interventions.

H. Methods of Treatment

Yet another aspect of the present invention provides methods of treatment for various medical conditions in mammals. The artisan will readily appreciate that the prodrugs of the invention are employed to treat diseases or disorders, or applied for diagnostic purposes that are the same or similar to the uses of the unmodified biologically effective compound.

The methods include administering to the mammal in need of such treatment, an effective amount of a prodrug, such as a 6-mercaptopurine PEG conjugate, which has been prepared as described herein. The compositions are useful for, among other things, treating neoplastic disease, reducing tumor burden, preventing metastasis of neoplasms, preventing recurrences of tumor/neoplastic growths in mammals. Further, a 6-mercaptopurine PEG conjugate has utility in modulating abnormal cell growth generally, and in particular, in treating and/or modulating autoimmune diseases and disorders, such as multiple sclerosis, and many other such art-known conditions.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, 6-mercaptopurine PEG conjugates are administered in amounts ranging from about 0.5 to about 3.0 mg/kg$^2$ per day, based on the molar proportion of the 6-mercaptopurine moiety per mg of prodrug.

The range set forth above is illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are administered to mammals in need thereof by various art-known parenteral routes.

To the extent that 6-mercaptopurine (6-MP) has been exemplified herein, it is mentioned that polymer conjugates of 6-MP according to the invention are readily employed to treat the same range of diseases or disorders for which unmodified 6-MP and/or the previously known prodrug of 6-MP, azathioprine, have been previously known to have some utility or potential.

I. EXAMPLES

The following examples serve to provide further appreciation of the invention but are not meant in any way to restrict the effective scope of the invention. The underlined and bold-faced numbers recited in the Examples correspond to those shown in the Figures.

Experimental

General. All reactions were run under an atmosphere of dry nitrogen or argon. Commercial reagents were used without further purification. All PEG compounds were dried under vacuum or by azeotropic distillation (toluene) prior to use. $^1$H spectra were obtained with a Varian MercuryVX-300 instrument using deuteriochloroform as solvent unless specified. $^{13}$C NMR spectra were obtained at 75.46 MHz on the Varian MercuryVX-300. Chemical shifts (δ) are reported in parts per million (ppm) downfield from tetramethylsilane (TMS) and coupling constants (J values) are given in hertz (Hz).

HPLC Method. Analytical HPLC's were performed using a size exclusion column (PolySep-GFC-P3000, Phenomenex) under isocratic conditions with a 1:1 mixture (v/v) of methanol-water as mobile phase. Peak elution was monitored at 254 nm using a UV detector. To detect the presence of any free PEG and also to confirm the presence of PEGylated product, an evaporative light scattering detector (ELSD), Model 5000 ELSD (Alltech), was employed. Based on ELSD and UV analysis, all the final PEGylated products were free of native drug and were ≧95% pure by BPLC.

Analysis of 6-mercaptopurine and 6-thioguanine content in PEG Derivatives. For the determination of the 6-mercaptopurine content in PEG derivatives, the UV absorbance of 6-mercaptopurine in 90% MeOH in H$_2$O (v/v) was determined at 277 nm for five different concentrations ranging from 0.02 μmol/mL to 0.10 μmol/mL. From the standard plot of absorbance vs. concentration, the absorption coefficient, ε, of 6-mercaptopurine was calculated to be 21.6 (O.D. at 277 nm for 1 mg/mL with 1.0 cm light path). PEGylated 6-mercaptopurine derivatives were dissolved in 90% MeOH in H$_2$O (v/v) at an approximate concentration of 0.006 μmol/mL (based on a MW of 40,000) and the UV absorbance of these compounds at 277 nm was determined. Using this value and employing the absorption coefficient, ε, obtained from the above, the concentration of 6-mercaptopurine in the sample was determined. Dividing this value by the sample concentration provided the percentage of 6-mercaptopurine in the sample. 6-TG samples were analyzed by the same method.

Determination of Rates of Hydrolysis of PEG Prodrugs. The rates of hydrolysis were obtained by employing a C8 reversed phase column (Zorbax® SB-C8) using a gradient mobile phase consisting of (a) 0.1 M triethylammonium acetate buffer and (b) acetonitrile. A flow rate of 1 mL/min was used, and chromatograms were monitored using a UV detector at 254 nm for 6-mercaptopurine. For hydrolysis in plasma, the derivatives were dissolved in acetonitrile at a concentration of 20 mg/mL. The solution was divided into vials with 100 µL and the solvent removed in vacuo. To the residue, 100 µL of plasma was added, then vortexed for 10 sec. The solutions were incubated at 37° C. for various periods of time. A mixture of methanol-acetonitrile (1:1, v/v,400 µL) was added to a vial at the proper interval and the mixture was vortexed for 1 min, followed by filtration through 0.45 mm filter membrane (optionally followed by a second filtration through 0.2 mm filter membrane). An aliquot of 40 µL of the filtrate was injected into the HPLC. On the basis of the peak area, the amounts of native compound and PEG derivative were estimated, and the half-life of each compound in different media was calculated using linear regression analysis from the disappearance of PEG derivative.

Abbreviations. DCM (dichloromethane), DMAP (4-(dimethylamino)pyridine), DMF (N,N-dimethylformamide), DSC (N,N'-disuccinimidyl carbonate), EDC (1-ethyl-3-(3-dimethylaminopropyl)carbodiimide), IPA (2-propanol), TBDMS-Cl (tert-butyl dimethyl silyl chloride), TFA (trifluoroacetic acid).

Example 1

Compound 4

A solution of 4-hydroxymethyl phenol (3, 9.3 g, 75 mmol) in DMF (50 mL) was flushed with anhydrous nitrogen gas for 10 minutes, followed by addition of TBDMS-Cl (12.44 g, 82 mmol). The reaction mixture was cooled to 0° C., followed by addition of solution of TEA (30.36 g, 300 mmol) in DMF (25 mL). The reaction solution was stirred overnight at room temperature and concentrated in vacuo. The residue was partitioned between water (100 mL) and DCM (200 mL) to extract the product into DCM twice. The organic layers were combined and dried over anhydrous $MgSO_4$ followed by removal of the solvent in vacuo to give the product 4 (16.3 g, 91%): $^{13}C$ NMR δ –5.344 (2 Si×$CH_3$), 18.285 (Si—C($CH_3$)$_3$), 25.850 (Si—C($CH_3$)$_3$), 64.840 (Ar—$CH_2$O), 115.221 (Ar—$C^2$), 127.842(Ar—$C^3$), 132.962 (Ar—$C^4$), 155.248 (Ar—$C^1$).

Example 2

Compound 7

Pyridine (983 mg, 12.43 mmol) was added to a suspension of 4 (2.7 g, 11.3 mmol) and DSC (3.18 g, 12.43 mmol) in $CHCl_3$ (140 mL) and the mixture was refluxed overnight followed by cooling to room temperature. Mono-Boc-diamine spacer(6, 3.398 g, 13.7 mmol) was added to the solution and the reaction mixture was stirred at room temperature overnight, followed by wash with 0.1N HCl (3×100 mL) and brine (100 mL). The organic layer was dried over anhydrous $MgSO_4$ and the solvent removed in vacuo. The residue was dissolved in hexane (100 mL) followed by filtration of insoluble impurities. The hexane filtrate was concentrated to give product 7 (5.1 g, 88%): $^{13}C$ NMR δ –5.469 (2×Si—$CH_3$), 18.235 (Si—C($CH_3$)$_3$), 25.790 (Si—C($CH_3$)$_3$), 28.263 (O—C($CH_3$)$_3$), 40.230 ($CH_2$NH), 40.917 ($CH_2$NH), 64.392 (Ar—$CH_2$O), 69.892 ($CH_2$O), 70.192 ($CH_2$O), 70.253 ($CH_2$O), 79.305 (OC($CH_3$)$_3$), 121.371 (Ar—$C^2$), 126.943 (Ar—$C^3$), 138.482 (Ar—$C^4$), 149.960 (OC(=O)NH), 154.936 (OC(=O)NH), 156.096 (Ar—$C^1$).

Example 3

Compound 8

Compound 7 (5 g, 9.76 mmol) was dissolved in acetonitrile (30 mL) and water (30 mL) followed by addition of HOAc (90 mL). The reaction mixture was stirred at room temperature for 1.5 hours, followed by the removal of the solvent. The residue was dissolved in DCM (300 mL), washed with water (3×300 mL), dried over anhydrous $MgSO_4$. The solvent was removed in vacuo to give the product 8 (4.1 g, 80%): $^{13}C$ NMR δ 28.233 (OC($CH_3$)$_3$), 40.184 ($CH_2$NH), 40.871 ($CH_2$NH), 64.484 (Ar—$CH_2$O), 69.811-70.191 (4×$CH_2$O), 79.228 (OC($CH_3$)$_3$), 121.661 (Ar—$C^2$), 127.950 (Ar—$C^3$), 138.177 (Ar—$C^4$), 150.418 (OC(=O)NH), 154.875 (OC(=O)NH), 156.111 (Ar—$C^1$).

Example 4

Compound 9

Thionyl chloride (314 mg, 2.64 mmol) was added to a solution of 8 (360 mg, 0.9 mmol) in pyridine (356 mg, 4.5 mmol) and DCM (30 mL) at 0° C. The mixture was stirred at 0-20° C. for 3 hours, followed by washing with water (3×30 mL). The organic layer was dried over anhydrous $MgSO_4$ and the solvent removed in vacuo to give the product 9 (320 mg, 85%): $^{13}C$ NMR δ 28.449, 40.385, 41.103, 45.680, 69.846, 70.295, 121.782, 129.513, 134.295, 150.872, 154.295, 155.833.

Example 5

Compound 10

EDC.HCl was added to a solution of 6-MP monohydrate (1, 1.66 g, 9.77 mmol) and $K_2CO_3$ (1.35 g, 9.77 mmol) in DMF (40 mL) and the mixture was stirred at room temperature for 1 hour, followed by addition of 9 (3.7 g, 8.88 mmol). The reaction mixture was stirred at room temperature for 4 hours, filtered, and the filtrate concentrated. The residue was purified by silica gel column chromatography (0-20% MeOH in $CHCl_3$, v/v) to give 0.7 g (15%) of product 10: $^{13}C$ NMR δ 28.442, 32.346, 40.397, 41.127, 69.979, 70.299, 79.592, 121.935, 130.319, 134.722, 141.890, 150.405, 151.900, 151.990, 155.126, 156.342. Anal. ($C_{24}H_{32}N_6O_6S$) C, H, N.

Example 6

Compound 11

Boc precursor (10, 180 mg, 0.34 mmol) was dissolved in DCM (4 mL) and TFA (2 mL) and the mixture stirred at room temperature for 2 hours. The solvent was removed in vacuo followed by addition of ether to precipitate a solid, which was washed with ether after filtration to give the product (175 mg, 95%): $^{13}C$ NMR ($CDCl_3$+$CD_3OD$) δ 15.142, 32.481, 39.518, 40.769, 40.891, 66.015, 66.656, 69.892, 69.984, 70.106, 70.152, 121.804, 130.199, 134.320, 142.547, 149.599, 150.332, 151.797, 155.521, 159.429.

Example 7

Compound 13

A solution of triethylamine (5 mL, 35.87 mmol) in DCM (5 mL) was added slowly to a solution of 4-hydroxy-3,5-dimethylbenzyl alcohol (12, 1.0 g, 6.58 mmol) and TBDMS- Cl (1.61 g, 10.7 mmol) in DCM (10 mL) at 0° C. over 1 hour. The final solution was let to warm to room temperature and stirred overnight at room temperature. TLC showed the completion of the reaction and the solvent was removed in vacuo and the residue was dissolved in DCM followed by washing with water four times to give 1.5 g (86%) of product 13: $^1$H NMR δ 0.00 (s, 6H, 2×CH$_3$), 0.84 (s, 9H, 3×CH$_3$), 2.11 (s, 6H, 2×Ar—CH$_3$), 4.50 (s, 3H, Ar—CH$_2$OH), 6.82 (s, 2H, 2×Ar—H); $^{13}$C NMR δ −3.25, 15.91, 18.48, 26.01, 64.91, 122.84, 126.93, 132.85, 151.15.

Example 8

Compound 15

Triphosgene (0.68 g, 1.91 mmol) and pyridine (0.949 g, 12 mmol) were added to a solution of 13 (1.33 g, 5.00 mmol) in chloroform (100 mL) and the mixture was stirred at room temperature for 6 hours followed by addition of 6 (5.0 g, 9.8 mmol). The mixture was stirred at room temperature overnight. The reaction solution was washed with 0.1 N HCl (3×10 mL), water (10 mL) and dried over anhydrous MgSO$_4$, followed by removal of the solvent in vacuo. The residue was purified by silica gel column chromatography (30 to 40% EtOAc in hexane) to give 2.5 g (93%) of product 15: $^{13}$C NMR δ −5.235 (2×Si—CH$_3$), 16.359, 18.483 (Si—C(CH$_3$)$_3$), 26.036, 28.455 (Si—C(CH$_3$)$_3$), 30.989 (O—C(CH$_3$)$_3$), 40.423 (CH$_2$NH), 41.178 (CH$_2$NH), 64.478 (Ar—CH$_2$O), 70.209 (CH$_2$O), 70.376 (CH$_2$O), 70.516 (CH$_2$O), 79.438 (OC(CH$_3$)$_3$), 126.402, 130.792, 138.639, 147.151, 154.486, 156.227 (Ar—Cs).

Example 9

Compound 16

Compound 15 was subjected to the condition in Example 3 to prepare 16 in 38% yield: $^{13}$C NMR δ 16.282, 28.442, 40.423, 41.204, 65.012, 70.171, 70.414, 70.516, 79.528, 127.439, 131.305, 138.345, 147.740, 154.409, 156.252.

Example 10

Compound 17

A mixture of 16 (800 mg, 1.88 mmol), Ph$_3$P (740 mg, 2.82 mmol), and CCl$_4$ (1.74 g, 11.28 mmol) in acetone (5 mL) and acetonitrile (5 mL) was stirred at room temperature overnight. The solvent was removed in vacuo and the residue purified by silica gel column chromatography (1:1 ethyl acetate-hexane, v/v) to give 400 mg (96%) of product 17: $^{13}$C NMR δ 14.213, 16.264, 28.412, 40.692, 41.193, 45.954, 70.055, 70.350, 70.462, 79.479, 128.832, 131.500, 134.562, 148.199, 153.958, 156.563.

Example 11

Compound 18

Compound 17 (0.4 g, 0.9 mmol) was added to a solution of 6-MP monohydrate (1, 0.17 g, 1.0 mmol) and K$_2$CO$_3$ (0.14 g, 1.0 mmol) in DMF (40 mL, by stirring for 1 hour) and the mixture was stirred at room temperature for 4 hours. The reaction mixture was filtered and the filter cake was washed with DCM. The filtrate was concentrated in vacuo and the residue was purified by silica gel column chromatography (0 to 10% MeOH in CHCl$_3$, v/v) to give 0.34 g (67%) of product 18: $^{13}$C NMR (CDCl$_3$+CD$_3$OD) δ 16.438, 16.460, 28.525, 40.477, 41.221, 70.321, 70.560, 79.872, 125.483, 128.508, 128.944, 129.604, 131.584, 132.258, 132.946, 147.651, 152.117.

Example 12

Compound 19

Compound 18 was subjected to the condition in Example 6 to prepare 19 in 95% yield. $^1$H NMR data confirmed the completion of the reaction.

Example 13

Compound 21

General Procedure

Boc-AA-OSu (20a-c, 6.5 mmol) was added to a solution of p-aminobenzyl alcohol (8.0 g, 6.5 mmol) in DCM (400 mL) and the solution stirred at room temperature overnight followed by cooling to −20° C. The precipitate was filtered and the filtrate was washed with water (200 mL), dried over anhydrous MgSO$_4$. The solvent was removed in vacuo and the residue recrystallized from hot EtOAc to give the product (21a-c).

Compound 21a. Prepared from Boc-gly-OSu in 75% yield: $^{13}$C NMR δ 25.437, 28.420, 45.175, 64.708, 67.217, 80.798, 120.479, 128.005, 137.081, 137.349, 156.959, 168.595, 172.725.

Compound 21b. Prepared from Boc-ala-OSu in 70% yield: $^{13}$C NMR δ 17.677, 18.407, 28.365, 50.881, 64.961, 80.859, 120.092, 127.951, 136.860, 137.500, 156.495, 171.472.

Compound 21c. Prepared from Boc-leu-OSu in 80% yield: $^{13}$C NMR δ 21.562, 22.919, 25.428, 28.218, 41.011, 53.345, 64.597, 80.315, 119.855, 127.586, 136.495, 137.379, 154.992, 156.592, 171.798.

Example 14

Compound 22

Prepared from 21a-c as described in example 4.

Compound 22a. Prepared from 21a in 80% yield: $^{13}$C NMR (CDCl$_3$+CD$_3$OD) δ 17.485, 18.816, 28.480, 46.260, 55.066, 80.051, 120.654, 129.845, 134.030, 138.587, 150.095, 169.372.

Compound 22b. Prepared from 21b in 75% yield: $^{13}$C NMR δ 17.331, 18.304, 27.469, 50.881, 52.878, 80.923, 120.053, 133.378, 138.281, 137.500, 156.572, 171.177.

Compound 22c. Prepared from 21c in 75% yield: $^{13}$C NMR δ 21.760, 23.053, 24.820, 28.391, 41.076, 46.119, 54.017, 80.641, 120.066, 139.397, 133.225, 138.332, 156.777, 172.086.

Example 15

Compound 23

Prepared from 22a-c as described in example 11 using 6-MP for M, 6-MPR for MR, and 6-TG for T compounds.

Compound 23aM. Prepared from 22a and 1 in 64% yield: $^1$H NMR (CDCl$_3$+CD$_3$OD) δ 1.468 (s, 9H, 3×CH$_3$), 3.868 (s, 2H, CH$_2$NH), 4.761 (s, 2H, CH$_2$S), 7.464 (ABq, 4H, J=23.0 Hz, 8.5 Hz, Ar—H), 7.675 (1H, NH), 8.227 (s, 1H, Ar—H of 6-MP), 8.729 (s, 1H, Ar—H of 6-MP); $^{13}$C NMR (CDCl$_3$+CD$_3$OD) δ 28.567, 33.047, 44.704, 49.030, 80.602, 120.896, 130.306, 133.986, 137.988, 152.454, 169.701.

Compound 23aT. Prepared from 22a and 2 in 58% yield: $^1$H NMR (CDCl$_3$+CD$_3$OD) δ 1.468 (s, 9H, Boc), 3.347 (s, 2H, NH$_2$), 3.875 (s, 2H, CH$_2$NH), 4.536 (s, 2H, CH$_2$S), 7.446 (ABq, 4H, J=25.75 Hz, 8.19 Hz, Ar—H), 7.648 (1H, Ar—H of purine), 7.804 (s, 1H, Ar—H of purine); $^{13}$C NMR (CDCl$_3$+CD$_3$OD) δ 28.525, 32.584, 44.662, 49.816, 80.602, 120.798, 130.208, 134.421, 137.693, 139.252, 157.679, 160.249, 169.561.

Compound 23bM. Prepared from 22b and 1 in 63% yield: $^{13}$C NMR (CDCl$_3$+CD$_3$OD) δ 18.560, 28.352, 32.692, 50.599, 80.500, 120.245, 120.501, 128.949, 149.499, 129.896, 133.262, 137.346, 142.031, 151.835, 156.277, 171.983.

Compound 23bMR. Prepared from 22b and 6-mercaptopurine riboside (1b) in 67% yield: $^{13}$C NMR (CDCl$_3$+CD$_3$OD) δ 17.782, 27.429, 27.654, 32.019, 50.205, 61.910, 62.025, 70.833, 73.608, 79.615, 85.500, 90.026, 119.941, 119.749, 129.077, 130.051, 131.231, 132.461, 136.678, 136.783, 142.564, 146.731, 150.546, 155.584, 161.025, 171.492.

Compound 23bT. Prepared from 22b and 2 in 21% yield: $^{13}$C NMR (CDCl$_3$+CD$_3$OD) δ 18.611, 28.468, 32.525, 42.060, 80.551, 120.603, 130.024, 134.094, 137.512, 139.368, 144.450, 156.559, 159.797, 172.687, 189.340.

Compound 23cM. Prepared from 22c and 1 in 50% yield: $^{13}$C NMR (CDCl$_3$+CD$_3$OD) δ 21.341, 22.570, 24.618, 27.895, 32.337, 41.361, 53.623, 79.876, 120.197, 129.516, 133.138, 137.157, 142.354, 151.622, 156.213, 157.032, 172.358.

Compound 23cT. Compound 22c and 2 are converted to 23cT.

Example 16

Compound 24

Prepared from 23a-c as described in example 6.

Compound 24aM. Prepared from 23aM in 95% yield. $^1$H NMR data confirmed the completion of the reaction.

Compound 24aT. Prepared from 23aT in 94% yield. $^1$H NMR data confirmed the completion of the reaction.

Compound 24bM. Prepared from 23bM in 99% yield. $^1$H NMR data confirmed the completion of the reaction.

Compound 24bMR. Prepared from 23bMR in 93% yield. $^1$H NMR data confirmed the completion of the reaction.

Compound 24bT. Prepared from 23bT in 97% yield. $^1$H NMR data confirmed the completion of the reaction.

Compound 24cM. Prepared from 23cM in 84% yield. $^1$H NMR data confirmed the completion of the reaction.

Compound 24cT. Compound 23cT is converted to 24cT.

Example 17

Compound 26

General Procedure

EDC.HCl (7.4 mmol) was added to a mixture of 24 (3.4 mmol), 25 (3.7 mmol), and DMAP (14.8 mmol) in anhydrous DCM (60 mL) and DMF (30 mL) at 0° C. and the mixture was stirred at 0° C. to room temperature overnight. The solvent was removed in vacuo and the residue redissolved in ethyl acetate to be washed with water (2·150 mL) and dried over anhydrous MgSO$_4$. The solvent was removed in vacuo and the residue purified by silica gel column chromatography to give 26.

Compound 26aM. Prepared from 24aM in 75% yield: $^{13}$C NMR (CDCl$_3$+CD$_3$OD) δ 28.528, 32.832, 40.632, 42.799, 70.365, 70.503, 70.731, 71.495, 79.783, 120.460, 130.107, 133.617, 137.616, 142.302, 152.147, 157.322, 167.701, 171.944.

Compound 26aT. Prepared from 24aT in 73% yield: $^{13}$C NMR (CDCl$_3$+CD$_3$OD) δ 28.512, 32.466, 40.647, 42.799, 70.380, 70.533, 70.716, 71.495, 79.798, 120.445, 130.061, 134.106, 137.479, 139.067, 157.352, 159.840, 167.732, 171.975.

Compound 26bM. Prepared from 24bM in 70% yield: $^{13}$C NMR (CDCl$_3$+CD$_3$OD) δ 18.880, 28.519, 32.820, 40.577, 40.679, 70.260, 70.388, 70.772, 71.438, 79.732, 120.501, 130.062, 133.659, 137.653, 142.197, 152.104, 148.301, 170.985, 171.279.

Compound 26bT. Prepared from 24bT in 75% yield: $^{13}$C NMR (CDCl$_3$+CD$_3$OD) δ 18.906, 28.557, 32.500, 40.743, 70.337, 70.465, 70.810, 71.489, 79.771, 120.565, 130.062, 134.210, 137.589, 139.010, 157.429, 159.887, 171.087, 171.407.

Compound 26cM. Prepared from 24cM in 71% yield: $^{13}$C NMR (CDCl$_3$+CD$_3$OD) δ 22.119, 23.040, 25.024, 28.532, 32.781, 40.525, 41.895, 52.071, 70.222, 70.952, 71.400, 79.720, 120.552, 130.127, 133.634, 137.666, 142.543, 152.169, 167.289, 171.100, 171.254, 171.318.

Compound 26cT. Compound 24cT is converted to 26cT.

Example 18

Compound 27

Prepared from 26 as described in example 6.

Compound 27aM. Prepared from 26aM in 90% yield. $^1$H NMR data confirmed the completion of the reaction.

Compound 27aT. Prepared from 26aT in 97% yield. $^1$H NMR data confirmed the completion of the reaction.

Compound 27bM. Prepared from 26bM in 85% yield. $^1$H NMR data confirmed the completion of the reaction.

Compound 27bT. Prepared from 26bT in 93% yield. $^1$H NMR data confirmed the completion of the reaction.

Compound 27cM. Prepared from 26cM in 94% yield. $^1$H NMR data confirmed the completion of the reaction.

Compound 27cT. Compound 26cT is converted to 24cT.

Example 19.

Compound 29.

A mixture of T-PEG (28, mw. 40,000, 5.0 g, 0.125 mmol), 11 (180 mg, 0.329 mmol), and DIEA (64.65 mg, 0.5 mmol) in anhydrous DCM (50 mL) was stirred at room temperature overnight. The solvent was removed in vacuo and the residue recrystallized from IPA (500 mL) twice to give the product 29 (4.5 g, 90%). The amount of 6-MP measured by UV assay was 0.74% wt/wt: $^{13}$C NMR δ 32.120, 38.539, 41.042, 42.850, 69.746-70.897(PEG), 121.543, 130.054, 134.562, 142.413, 150.194, 151.795, 154.632, 170.025.

Example 20

Compound 31

General Procedure

EDC.HCl (0.8 mmol) was added to a mixture of PEG-cmc-aspartic-OH (30, 0.05 mmol), TFA NH$_2$-spacer 6-MP (11, 19, or 27, 0.4 mmol), and DMAP (1.6 mmol) in anhydrous DCM (15 mL) and DMF (5 mL) at 0° C. and the mixture was stirred at 0° C. to room temperature overnight. The solvent was removed in vacuo and the residue recrystallized from IPA to give product 31.

Compound 31a. Prepared from 11 in 90% yield. The amount of 6-MP measured by UV assay was 1.27% wt/wt: $^{13}$C NMR δ 32.022, 37.331, 39.185, 40.968, 49.578, 61.544, 69.437-70.869 (PEG), 121.585, 130.517, 134.590, 142.146, 149.112, 150.194, 151.753, 154.800, 159.379, 170.376, 170.643.

Compound 31b. Prepared from 19 in 94% yield: $^{13}$C NMR (CDCl$_3$+CD$_3$OD) δ 16.995, 38.778, 40.253, 41.025, 41.826, 43.792, 53.090, 54.115, 65.379, 70.350, 70.435-71.334 (PEG), 129.169, 132.821, 133.945, 148.635, 149.225, 156.037, 171.992, 172.975.

Compound 31c. Prepared from 27aM in 87% yield. The amount of 6-MP measured by UV assay was 1.45% wt/wt: $^{13}$C NMR (CDCl$_3$+CD$_3$OD) δ 31.846, 37.155, 38.686, 38.789, 38.897, 47.408, 51.467, 16.798, 68.728-70.399 (PEG), 119.443, 119.527, 129.162, 132.575, 136.620, 151.212, 155.903, 166.928, 167.026, 170.383, 170.917, 170.973, 171.436.

Compound 31d. Prepared from 27aT in 88% yield. The amount of 6-TG measured by UV assay was 1.42% wt/wt: $^{13}$C NMR (CDCl$_3$+CD$_3$OD) δ 31.187, 37.029, 38.532, 38.616, 39.094, 41.678, 51.147, 63.615, 66.214, 68.545-71.832 (PEG), 119.274, 119.359, 128.923, 133.038, 133.277, 136.381, 136.451, 138.529, 155.832, 158.852, 166.914, 166.998, 170.242, 170.902, 171.338.

Compound 31e. Prepared from 24bM in 88% yield. The amount of 6-MP measured by UV assay was 1.46% wt/wt: $^{13}$C NMR (CDCl$_3$+CD$_3$OD) δ 17.626, 17.724, 32.766, 38.272, 52.443, 64.760, 69.675-71.459 (PEG), 120.713, 129.955, 133.480, 133.564, 137.848, 137.932, 143.213, 152.202, 157.145, 159.477, 171.358, 171.808, 171.934, 172.299.

Compound 31f. Prepared from 24bMR in 95% yield. The amount of 6-MP measured by UV assay was 1.44% wt/wt: $^{13}$C NMR (D$_2$O) δ 19.532, 34.450, 52.079, 54.339, 54.046, 67.007, 71.566, 72.014-74.867 (PEG), 76.486, 80.390, 91.165, 122.918, 132.061, 132.865. 135.511, 139.115, 145.478, 149.278, 153.751, 158.536, 163.961, 173.007, 174.921.

Compound 31 g. Prepared from 27bM in 90% yield. The amount of 6-MP measured by UV assay was 1.46% wt/wt: $^{13}$C NMR (CDCl$_3$+CD$_3$OD) δ 18.454, 32.283, 38.853, 51.530, 40.703, 63.848, 65.359, 67.145, 68.091-71.893 (PEG), 119.117, 128.611, 132.045, 134.335, 136.075, 141.051, 150.469, 155.063, 169.396.

Compound 31h. Prepared from 27bT in 88% yield. The amount of 6-TG measured by UV assay was 1.32% wt/wt: $^{13}$C NMR (CDCl$_3$+CD$_3$OD) δ 18.792, 32.275, 37.991, 39.564, 52.232, 64.605, 69.535-71.136 (PEG), 120.348, 120.475, 129.955, 134.014, 134.252, 137.413, 139.449, 156.752, 159.701, 170.993, 171.331, 172.285.

Compound 31i. Prepared from 27cM in 85% yield. The amount of 6-MP measured by UV assay was 1.17% wt/wt: $^{13}$C NMR (CDCl$_3$+CD$_3$OD) δ 20.260, 21.566, 23.757, 30.962, 38.237, 40.554, 50.737, 59.922, 61.776, 62.675, 63.236, 67.085-71.396 (PEG), 119.176, 128.544, 132.476, 136.535, 141.984, 150.706, 160.607, 169.905.

Compound 31j. 27cT is converted to compound 31j by the same procedure.

Example 21

Compound 33

EDC.HCl (461 mg, 2.4 mmol) was added to a mixture of PEG-cmc-aspartic-aspartic-OH (32, 4.0 g, 0.1 mmol), 27bM (800 mg, 1.2 mmol), and DMAP (586 mg, 4.8 mmol) in anhydrous DCM (50 mL) and DMF (5 mL) at 0° C. and the mixture was stirred at 0° C. to room temperature overnight. The solvent was removed in vacuo and the residue recrystallized from IPA to give product 33 (3.5 g, 88%). The amount of 6-MP measured by UV assay was 2.57% wt/wt: $^{13}$C NMR (CD$_3$Cl+CD$_3$OD) δ 18.876, 24.016, 30.814, 32.878, 37.808, 39.845, 64.928, 69.802-71.431 (PEG), 120.784, 130.222, 134.028, 137.946, 143.115, 152.356, 171.443, 171.822.

Example 22

In Vitro Experiment

Cell Lines and Cytotoxicity Assays. Studies using P388/0 cell lines for IC$_{50}$ (drug concentration inhibiting growth of cells by 50%) were maintained and conducted as previously reported. Briefly, for IC$_{50}$ determination, cells were seeded into the microwell plates at a density of 2×10$^3$ cells per 50 μL per well. Plates were incubated at 37° C. in a humidified incubator with 5% CO$_2$ for 3 days. Cell growth was measured by the addition of 10 μL/well of Alamar Blue (Alamar Biosciences, Inc., Sacramento, Calif.) and the plates were incubated a further 4 hours at 37° C. The IC$_{50}$ values for each compound were determined from absorbance versus dilution factor plots. All cell cultures for animal implantation were maintained at 37° C. in a humidified atmosphere of 5% CO$_2$/95% O$_2$ and subcultured once a week. All cell lines were periodically tested for Mycoplasma and were Mycoplasma free. The results are shown in Table 1.

TABLE 1

In vitro results of 6-MP and Its PEG Derivatives.

| Compound | t½ in PBS, pH 7.4 | t½ in rat plasma at 37° C. | t½ in human plasma at 37° C. | Solubility in water (mg/mL) | IC$_{50}$ (P388/0, μM) |
|---|---|---|---|---|---|
| 6-MP (1) | — | — | — | <0.1 | 2.67 |
| 6-TG (2) | — | — | — | — | 0.36 |
| 29 | >24 h | 2.0 h | 1.5 h | — | 11.6 |
| 31a | >24 h | 0.69 h | 0.7 h | — | no inhibition |
| 31c | >24 h | >24 h | >24 h | 180 | no inhibition |
| 31d | >24 h | >24 h | >24 h | — | no inhibition |
| 31e | >24 h | >24 h | >24 h | 186 | no inhibition |
| 31f | >24 h | >24 h | >24 h | 181 | no inhibition |
| 31g | >24 h | >24 h | >24 h | — | no inhibition |
| 31h | >24 h | >24 h | >24 h | — | no inhibition |
| 31i | >24 h | 15.2 h | 18.4 h | 272 | no inhibition |
| 33 | >24 h | >24 h | >24 h | 114 | no inhibition |

Example 23

In vivo Experiment with M109 Tumor Model

M109 cells (NCI), derived from donor mice, were grown and expanded in tissue culture for in vivo implantation. Cells were grown in EMEM with 10% FBS and 1% streptomycin/penicillin media, kept in an incubator at 37° C. with 5% CO$_2$ and split twice a week. Cells were trypsinized, harvested, washed, counted and prepared in PBS for transport to the vivarium. Cells were kept on ice until implantation was conducted with minimum lag time. A cell suspension of approximately 5×10$^6$ cells/mL was used. Balb/C mice were implanted subcutaneous with 100 μL of the above cell suspension (Day 0). Treatments were administered intravenously on Day 1 and Day 4. Compound doses were based on the content of 6-MP. Body weight and tumor volume were then measured twice weekly until the group's median tumor volume exceeded 2000 mm³. The tumor volume for each mouse was determined by measuring two dimensions with calipers and calculated using the formula: tumor volume= (length×width²)/2. Drug effects were determined by comparing tumor growth in treated versus control (no vehicle) mice. Two types of endpoints were used as the basis for comparison: (a) the percent difference in tumor volume (% T/C), measured when the control group's median tumor volume reached approximately 800-1100 mm³ (exponential growth phase) and (b) again when the control group's median tumor volume was approximately 2000 mm³.

Results

Unmodified 6-MP was ineffective at inhibiting the growth of M109 solid tumors. In contrast, some PEG-6-MP conjugates caused roughly an 80% reduction in tumor growth as compared to control (Table 2). A similar enhancement of anti-tumor activity was produced with PEG conjugation of 6-TG.

TABLE 2

Efficacy Comparison Between 6-MP And PEG-MP$^\alpha$ Against Lung M109 Syngeneic Solid Tumors In Balb/C Mice.

| Compound | Total Dose (mg/kg) | T/C (%)$^x$ at Day 18 | T/C (%)$^x$ at Day 25 |
|---|---|---|---|
| 6-MP (1) | 200 | 144 | 184 |
| 6-TG (2) | 40 | 82 | 78 |
| 29 | 200 | 144 | 184 |
| 31a | 60 | 28 | 38 |
| 31c | 60 | 108 | 92 |
| 31d | 60 | Toxic | Toxic |
| 31e | 60 | 21 | 54 |
| 31f | 60 | 26.5 | 35.0 |
| 31g | 60 | 43.8 | 70.7 |
| 31h | 60 | 9 | 27 |
| 31i | 60 | 136 | 71 |
| 33 | 60 | 84 | 60 |

$^\alpha$All PEG compounds were given day 1 & 4, i.v.
$^x$The median tumor volume of treatment and control groups were measured and compared when the control group's median tumor volume reached approximately 1000 mm³ (day 18) and 2000 mm³ (day 25).

Example 24

In vivo Experiment with L1210 Tumor Model

6-MP and pro-drug forms of 6-MP were screened for in vivo activity against the murine leukemia cell line L1210/O (mouse, lymphocytic leukemia). The cell line was obtained from Southern Research Institute (Birmingham, Ala.) and grown in DMEM supplemented with 10% horse serum. L 1210/O cells were subcultured two times per week and log phase cultures (viability≧95%) were used for all in vivo experiments. Female CD2F1 mice (Taconic Farms, Germantown, N.Y.) at 7-8 weeks of age were used for study. Following one week of acclimation, mice were implanted i.p. with L1210/0 cells (5×10⁵ cells/mouse) at designated day 0. The mice were randomly assigned to experimental groups (8-10/group). The groups included control, 6-MP and PEG-6-MP conjugates. 6-MP was solubilized in 3% DMSO and suspended in intralipid and administered Q2d×6, IP. PEG-6-MP was dissolved in phosphate buffer (pH 5.8) and administered Q4d×3, IV. Control groups received vehicle (intralipid or phosphate buffer). The mice were monitored for up to 40 days, and the treatment was evaluated as percentage of increase in life span (ILS).

Results

The PEG-6-MP conjugate (31a) showed significantly (P<0.05) greater survival in this ascites model (Table 3) than both vehicle control and the 6-MP matched dose equivalent.

TABLE 3

Efficacy Comparison of PEG-6MP Analog Against a Murine Leukemia (L1210/0) Ascites Model

| Compound | Total Dose (mg/kg) | % ILS$^\alpha$ |
|---|---|---|
| 6-MP (1) | 90 | 31.8 |
|  | 240 | 52.5* |
| 29 | 90 | 27.4 |
| 31a | 90 | 70.2*+ |
| 31c | 90 | 48.1* |
| 31e | 90 | 54.7* |
| 31i | 90 | 8.9 |
| 33 |  |  |

$^\alpha$Percent increase in life span (% ILS) was calculated from the quotient of the treatment group mean survival divided by the control group mean survival [(T/C−1) × 100].
*Significant (P < 0.05) vs. untreated control group.
+Significant (P < 0.05) vs. 6-MP matched treatment.

What is claimed is:

1. A compound of the formula

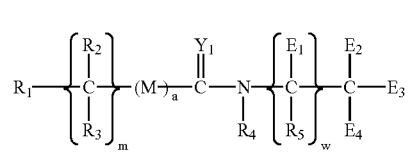

(Ib)

wherein:
R$_1$ is a polymeric residue having an average molecular weight of from about 2,000 to about 100,000;
Y$_1$ is O, S or NR$_{10}$;
M is O, S or NR$_{11}$;
E$_1$ is

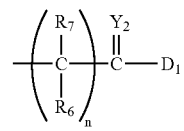

E$_{2-4}$ is are independently H, E$_1$ or

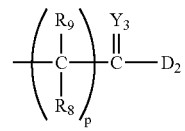

(a) is zero or one;
(m) is zero or a positive integer,
(w) is zero or one;
(n) and (p) are independently 0 or a positive integer;
Y$_{2-3}$ are independently O, S or NR$_{12}$;
R$_{2-11}$ and R$_{15}$ are independently selected from the group consisting of hydrogen, C$_{1-6}$alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $D_1$ and $D_2$ are independently OH,

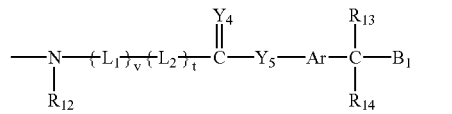
(IV)

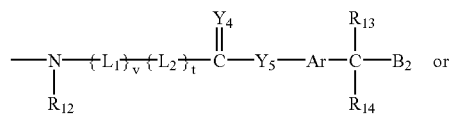
(V)

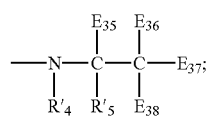
(VI)

wherein:

$R'_4$ and $R'_5$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$E_{35}$ is

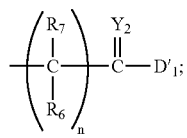

$E_{36-38}$ are independently H, $E_{35}$, or

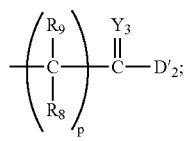

and $D'_1$ and $D'_2$ are independently OH,

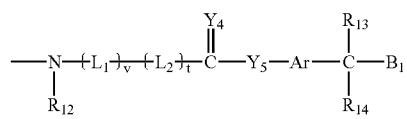
(IV)

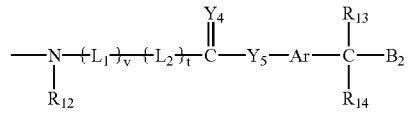
(V)

or,

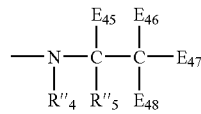
(VII)

wherein:

$R''_4$ and $R''_5$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$E_{45}$ is

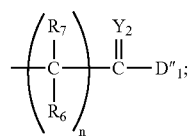

$E_{46-48}$ are independently H, $E_{45}$, or

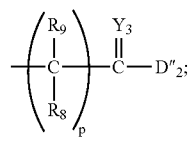

and $D''_1$ and $D''_2$ are independently OH,

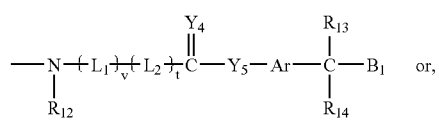
(IV)

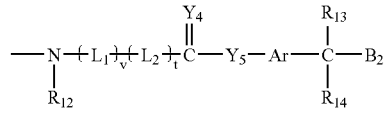
(V)

(v) and (t) are independently 0 or 1;

$L_1$ and $L_2$ are independently selected linkers;

$Y_{4-5}$ are independently selected from the group consisting of O, S and $NR_{16}$;

$R_{12-14}$ and $R_{16}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is a moiety which when included in Formula (Ib) forms a multisubstituted aromatic hydrocarbon or a multi-substituted heterocyclic group; and $B_1$ and $B_2$ are independently selected from the group consisting of OH, and residues of sulfhydryl-containing moieties

[Structure: E2, E3, E4 attached to central C]

provided that w is not zero when is $CH_2COOH$.

2. The compound of claim 1, wherein a terminal end of $R_1$ includes a cap group, which is selected from the group consisting of hydrogen, $NH_2$, OH, $CO_2H$, $C_{1-6}$ moieties and (Ib')

[Structure showing: $E_3-C(E_2)(E_4)-C(E_1)(R_5)-N(R_4)-C(=Y_1)-(M)_a-[C(R_2)(R_3)]_m-$]

wherein all variables are as previously defined.

3. A compound of claim 2, of the formula:

(IIIb)

[Structure: $E_3-C(E_2)(E_4)-C(E_1)(R_5)-N(R_4)-C(=Y_1)-(M)_a-[C(R_2)(R_3)]_m-R_1-[C(R_2)(R_3)]_m-(M)_a-C(=Y_1)-N(R_4)-C(R_5)(E_1)-C(E_2)(E_4)-E_3$]

4. The compound of claim 1, wherein $Y_1$-$Y_5$ are each O.

5. The compound of claim 1, wherein $R_1$ comprises a polyalkylene oxide residue.

6. The compound of claim 5, wherein $R_1$ comprises a polyethylene glycol residue.

7. The compound of claim 1, wherein $R_1$ is selected from the group consisting of:

—C(=Y')—$(CH_2)_{n3}$—O—$(CH_2CH_2O)_x$—$A_2$,

—C(=Y')—Y"—$(CH_2)_{n3}$—O—$(CH_2CH_2O)_x$—$A_2$, and

C(=Y')—$NR'_6$—$(CH_2)_{n3}$—O—$(CH_2CH_2O)_x$—$A_2$, wherein:

x is the degree of polymerization;

n3 is zero, or a positive integer;

$R'_6$ is selected from the group which defines $R_6$;

Y' and Y" are independently O or S;

$A_2$ is a capping group.

8. The compound of claim 7, wherein $R_1$ comprises —O—$(CH_2CH_2O)_x$ and x is a positive integer so that the weight average molecular weight is at least about 20,000.

9. The compound of claim 1, wherein $R_1$ has a weight average molecular weight of from about 5,000 to about 50,000.

10. The compound of claim 1, wherein $B_1$ and $B_2$ are independently selected residues of SH-containing moieties.

11. The compound of claim 10, wherein said SH-containing moieties are selected from the group consisting of 1-β-D-ribofuranosyl, 1-β-D-arabinofuranosyl, penicillamine, 2-thiouracil, captopril, tiopronin, vasopressin, deaminooxytocin, thiopental sodium, and

[Structure: bicyclic ring system with S substituent, $R_{31}$, $R_{30}$, $X_3$]

wherein $R_{30}$ is one of H, a $C_{1-6}$ alkyl, alkoxy, or a carbohydrate of the formula:

[Sugar ring structure with $R_{32}$, $R_{33}$, $R_{34}$, $R_{35}$, $R_{36}$]

wherein $R_{32-36}$ are independently selected from alkoxy, $OR_{37}$, H, OH, $N_3$, $NHR_{38}$, $NO_2$, CN, fluoro, chloro, bromo, or iodo, wherein $R_{37-38}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, halo, substituted aryls, aralkyls, $C_{1-6}$ heteroalkyls and substituted $C_{1-6}$ heteroalkyls;

$R_{31}$ is H or $NH_2$; and $X_3$ is CH or N.

12. The compound of claim 1, wherein $L_1$ is $(CH_2CH_2O)_2$.

13. The compound of claim 1, wherein $L_2$ is selected from the group consisting of —$CH_2$—, —$CH(CH_3)$—, $CH[CH_2CH(CH_3)_2]$—, —$CH_2C(O)NHCH(CH_3)$—, —$(CH_2)_2$—, —$CH_2C(O)NHCH_2$—, $CHC(O)NHCH$ $[CH_2CH(CH_3)_2]$, —$(CH_2)_2$—NH— and —$(CH_2)_2$—NH—$C(O)(CH_2)_2NH$—.

14. A compound of claim 2, selected from the group consisting of:
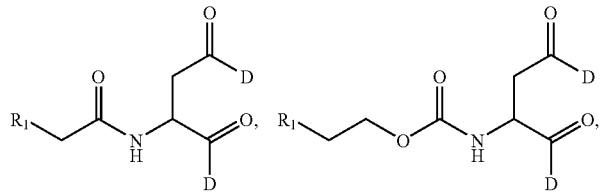
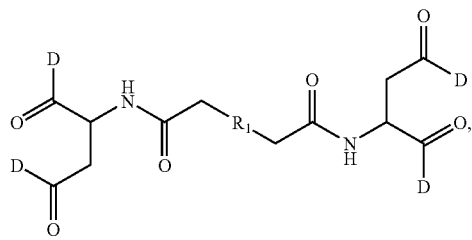
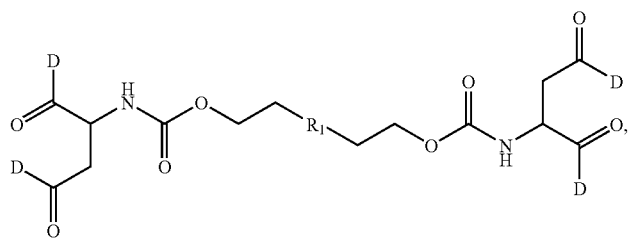
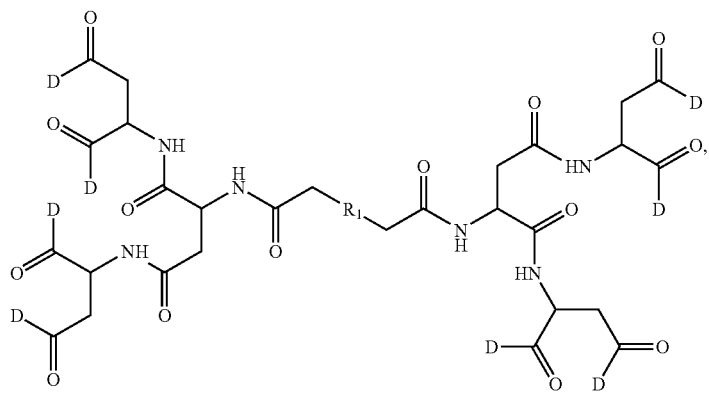
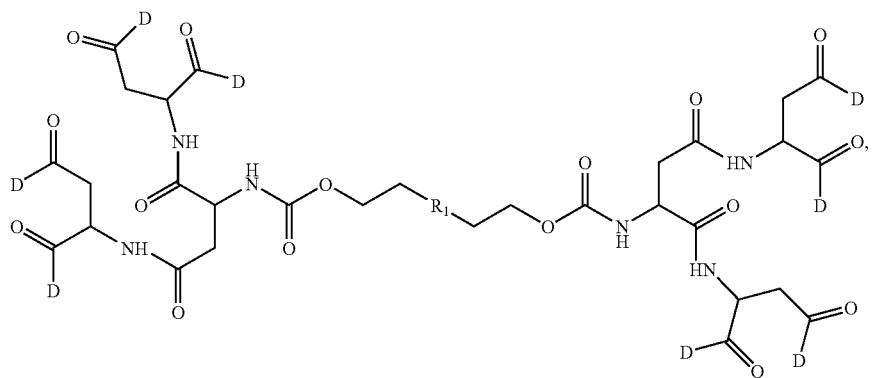

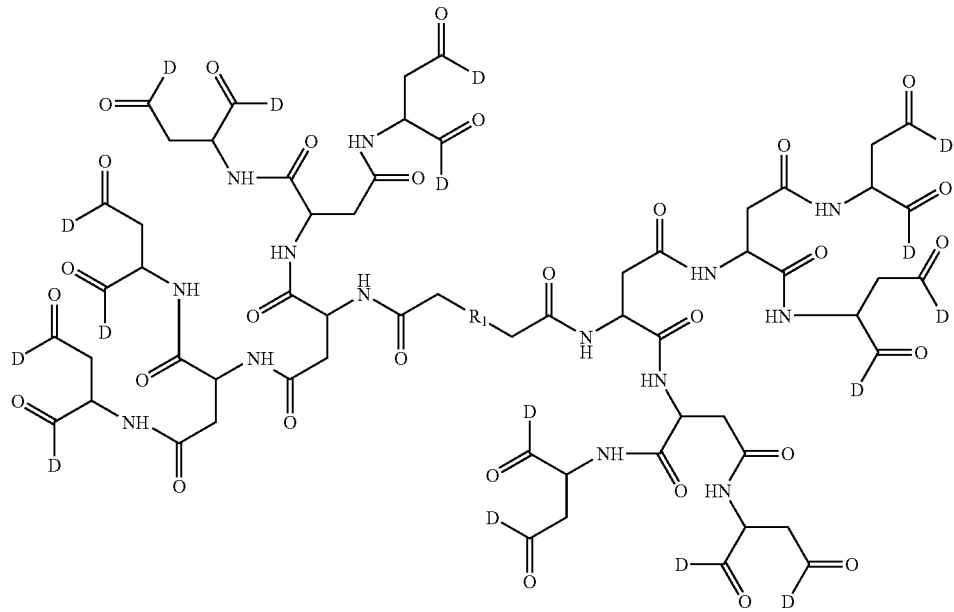
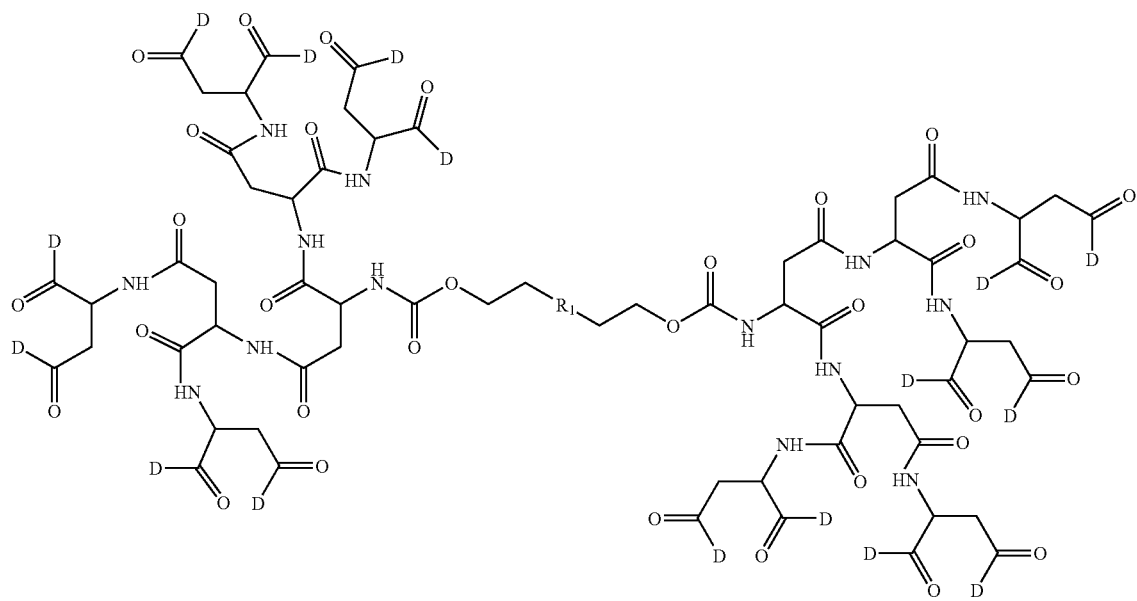
wherein $R_1$ is a straight or branched residue of a water soluble polymer and D is selected from the group comprising:
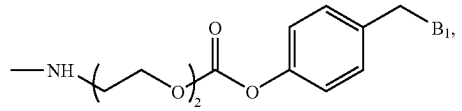
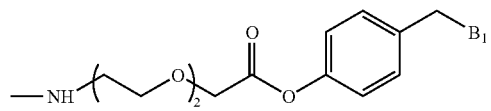
-continued
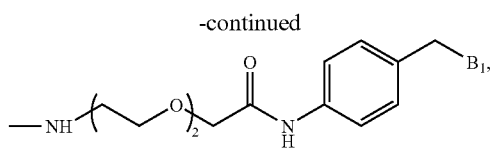
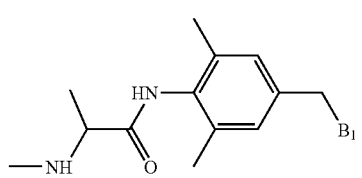

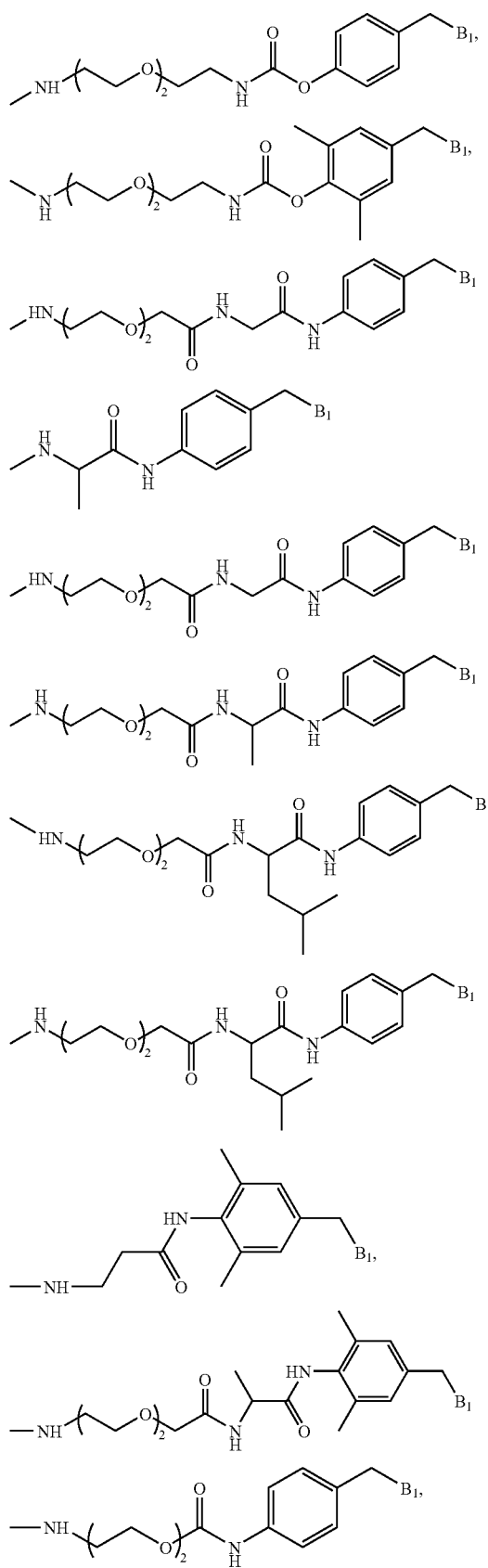
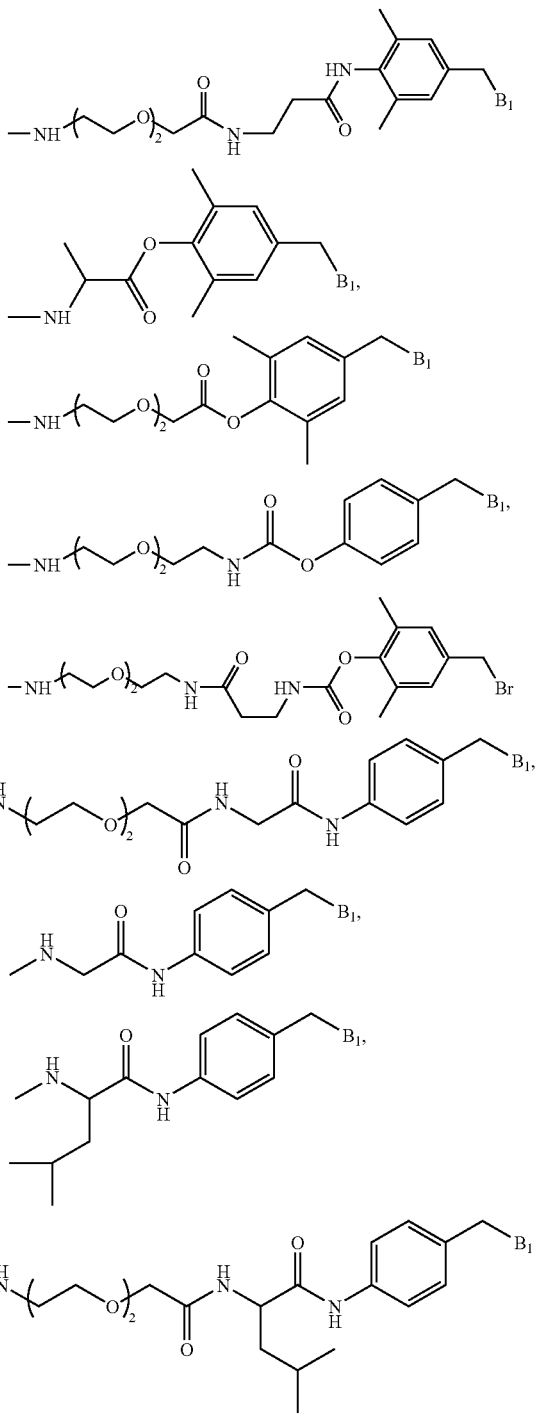
wherein $B_1$ are residues of a SH-containing moiety.
15. The compound of claim 1, wherein $R_1$ is a water soluble polymer.
16. The compound of claim 1, wherein w is not zero when $E_{2-4}$ are each H and $D_1$ and $D_2$ are both not simultaneously OH.
* * * * *

UNITED STATES PATENT AND TRADEMARK OFFICE
CERTIFICATE OF CORRECTION

PATENT NO. : 7,262,164 B2
APPLICATION NO. : 10/290694
DATED : August 28, 2007
INVENTOR(S) : Yun H. Choe et al.

It is certified that error appears in the above-identified patent and that said Letters Patent is hereby corrected as shown below:

a) Column 35, lines 1-10,
"
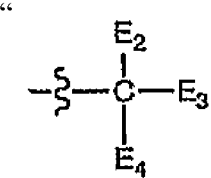

provided that w is not zero when
is $CH_2COOH$." should appear as follows:

-- provided that w is not zero when

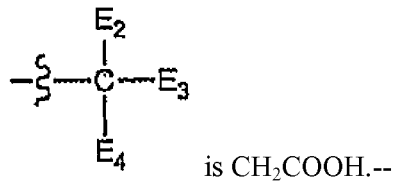   is $CH_2COOH$.-- b) Column 35, lines 11-25,
claim 2 should read as follows:
--The compound of claim 1, wherein a terminal end of $R_1$ includes a cap group, which is selected from the group consisting of hydrogen, $NH_2$, OH, $CO_2H$, $C_{1-6}$ moieties and $E_1$-                                                          (Ia')

or

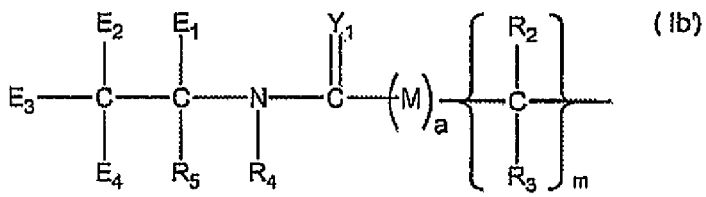                                      (Ib')

wherein all variables are as previously defined.--

UNITED STATES PATENT AND TRADEMARK OFFICE
CERTIFICATE OF CORRECTION

PATENT NO. : 7,262,164 B2  
APPLICATION NO. : 10/290694  
DATED : August 28, 2007  
INVENTOR(S) : Yun H. Choe et al.

Page 2 of 2

It is certified that error appears in the above-identified patent and that said Letters Patent is hereby corrected as shown below:

c) <u>Column 42, lines 25-30,</u>  
the compound should appear as follows:

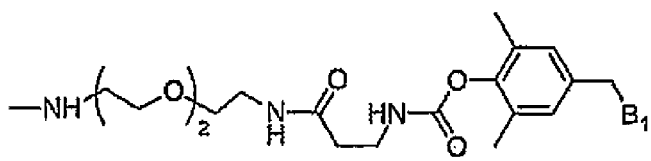

Signed and Sealed this

Twentieth Day of November, 2007

JON W. DUDAS  
*Director of the United States Patent and Trademark Office*